(12) United States Patent
Sasaki et al.

(10) Patent No.: US 8,592,643 B2
(45) Date of Patent: Nov. 26, 2013

(54) METHODS FOR INTRODUCING A HUMAN GENE INTO A MARMOSET EMBRYO FOR MAKING A TRANSGENIC MARMOSET

(75) Inventors: Erika Sasaki, Kanagawa (JP); Hideyuki Okano, Tokyo (JP)

(73) Assignees: Central Institute for Experimental Animals, Kawasaki-shi (JP); Keio University, Tokyo (JP)

( * ) Notice: Subject to any disclaimer, the term of this patent is extended or adjusted under 35 U.S.C. 154(b) by 256 days.

(21) Appl. No.: 12/865,304

(22) PCT Filed: Dec. 9, 2008

(86) PCT No.: PCT/JP2008/072732
§ 371 (c)(1),
(2), (4) Date: Nov. 15, 2010

(87) PCT Pub. No.: WO2009/096101
PCT Pub. Date: Aug. 6, 2009

(65) Prior Publication Data
US 2011/0055939 A1    Mar. 3, 2011

(30) Foreign Application Priority Data
Jan. 29, 2008 (JP) .................................. 2008-017955

(51) Int. Cl.
*A01K 67/00* (2006.01)
(52) U.S. Cl.
USPC .................................. 800/8; 800/18; 800/21
(58) Field of Classification Search
USPC ................................................. 800/8, 21, 18
See application file for complete search history.

(56) References Cited

U.S. PATENT DOCUMENTS

| 6,291,740 B1 | 9/2001 | Bremel et al. |
| 2001/0044937 A1 | 11/2001 | Schatten et al. |

FOREIGN PATENT DOCUMENTS

| JP | 10 185919 | 7/1998 |
| JP | H10-185919 | * 7/1998 |
| JP | 2003 533973 | 11/2003 |
| JP | 2003-533973 | * 11/2003 |
| JP | 2004 147604 | 5/2004 |
| WO | 90 08832 | 8/1990 |
| WO | WO2006/029093 | * 3/2006 ............... C12N 5/06 |

OTHER PUBLICATIONS

JP 2003-533973 translation, 2003.*
Mullins (1990, Nature, vol. 344, p. 541-544).*
Hammer (1990, Cell, vol. 63, p. 1099-1112).*
Mullins, 1989, EMBO, vol. 8, p. 4065-4072.*
Taurog, 1988, J. Immunol., vol. 141, p. 4020-4023.*
Scarff (genesis, 2003, vol. 36, p. 149-157).*
Kirik (PNAS, 2003, vol. 100, No. 5, p. 2884-2889).*
Rubinsztein (Trends Genetics, 2002, vol. 18, No. 4, p. 202-209).*
Theuring (Trends Biotechnol., 1997, vol. 15, No. 8, p. 320-325).*
Price (Science, 1998, vol. 282, No. 5391, p. 1079-1083).*
Chan, A. W. S. et al., "Transgenic Monkeys Produced by Retroviral Gene Transfer Into Mature Oocytes", Science, vol. 291, No. 5502, pp. 309-312 (Jan. 12, 2001).
Kirik, D. et al., "Nigrostriatal Alpha-Synucleincpathy Induced by Viral Vector-Mediated Overexpression of Human Alpha-Synuclein: A new Primate Model of Parkinson's Disease", Proc Natl Acad Sci, vol. 100, No. 5, pp. 2884-2889 (Mar. 4, 2003).
Price, D. L., et al, "Genetic Neurodegenerative Diseases: The Human Illness and Transgenic Models", Science, vol. 282 pp. 1079-1083 (Nov. 6, 1998).
Rubinsztein, D. C. "Lessons From Animal Models of Huntington's Disease", Trends in Genetics, vol. 18, No. 4, pp. 202-209 (Apr. 2002).
Theuring, F. et al. "Transgenic Animals As Models of Neurodegenerative Diseases in Humans", Tibtech, vol. 15, pp. 320-325 (Aug. 1997).
Extended Search Report issued Jan. 23, 2013 in European Application No. 08871871.3.
Shang-Hsun Yang, et al., "Towards a transgenic model of Huntington's disease in a non-human primate", Nature, vol. 453, No. 7197, Jun. 12, 2008, pp. 921-924.
Erika Sasaki, et al., "Generation of trangenic non-human primates with germline transmission", Nature, vol. 459, No. 7246, May 28, 2009, pp. 523-527.
Gerald Schatten, et al., "Trangenic primate offspring", Nature, vol. 459, No. 7246, May 28, 2009, pp. 515-516.
David Cyranoski, "Marmoset model takes centre stage", Nature, vol. 459, No. 7246, May 28, 2009, p. 492.
Editor Nature, "Time to connect", Nature, vol. 459, No. 7246, May 28, 2009, p. 483.
Japanese Office Action in corresponding Application No. 2009-551406 dated Apr. 2, 2013.
N. Nishimura, Success in producing a first potential practically useful primate, "transgenic marmost", [online], Sep. 10, 2009, internet cite <http:www.natureasia.com/ja-jp/nature/interview/contens/1>.
E. Sasaki, Production of a genetically-modified primate, LABIO21, No. 38, Oct. 2009.

* cited by examiner

*Primary Examiner* — Michael C. Wilson
(74) *Attorney, Agent, or Firm* — Oblon, Spivak, McClelland, Maier & Neustadt, L.L.P.

(57) ABSTRACT

An object of the present invention is to provide a method for introducing a gene into an embryo for production of a human disease model primate animal using a non-human primate animal such as a marmoset. The present invention relates to a method for introducing a foreign gene into an early embryo of a non-human primate animal, which comprises placing early embryos of a non-human primate in a 0.2 M to 0.3 M sucrose solution, so as to increase the volume of the perivitelline spaces, and then injecting a viral vector containing a human foreign gene operably linked to a promoter into the perivitelline spaces of the early embryos.

5 Claims, 17 Drawing Sheets

A

N461① 2.5 Day    N461① 3.5 Day    N461① 8.5 Day

B

N461② 2.5 Day    N461② 3.5 Day    N461② 8.5 Day

No. 587 Wakaba

No. 594 Kei / No.666 Kou

No. 584 Hisui

No. 588 Banko

| Sample Name | Specimen | 2463TH-FAM | CJ081-VIC | | CJ103-NED | | | CJ003-NED | | CJ091-FAM | | Determination |
|---|---|---|---|---|---|---|---|---|---|---|---|---|
| I2343 | Hair | 108.8 | 159.5 | 186.2 | 115 | | | 93.8 | 97.7 | 138.8 | | Recipient |
| I2353 | Hair | 108.8 | 186.2 | | 115 | | | 93.8 | 97.7 | 138.7 | | Recipient |
| I2991 | Hair | 108.7 | 167.8 | 169.9 | 117.1 | 119.1 | | 93.8 | | 138.8 | | Donor |
| IH555 | Hair | 108.7 | 163.7 | 165.7 | 117.1 | | 125.5 | 86 | 93.7 | 138.9 | 145.4 | Donor |
| I2343 offspring 1 | Hair | 108.7 | 163.6 | 169.8 | 117.1 | | | 86 | 93.7 | 138.9 | 145.3 | offspring of Donor |
| I2343 offspring 2 | Hair | 108.7 | 163.6 | 169.8 | 117 | | | 86 | 93.7 | 138.9 | 145.3 | offspring of Donor |

SEQUENCE LISTING

<160> NUMBER OF SEQ ID NOS: 19

<210> SEQ ID NO 1
<211> LENGTH: 28
<212> TYPE: DNA
<213> ORGANISM: Artificial
<220> FEATURE:
<223> OTHER INFORMATION: primer

<400> SEQUENCE: 1
gcacaagctg gagtacaact acaacagc                                          28

<210> SEQ ID NO 2
<211> LENGTH: 22
<212> TYPE: DNA
<213> ORGANISM: Artificial
<220> FEATURE:
<223> OTHER INFORMATION: primer

<400> SEQUENCE: 2
tcacgaactc cagcaggacc at                                                22

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
tcctgaccct gaagtacccc                                                   20

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
gtggtggttg aagctgtagc c                                                 21

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
ctggtcgagc tggacggcga cg                                                22

```
<210> SEQ ID NO 6
<211> LENGTH: 22
<212> TYPE: DNA
<213> ORGANISM: Artificial
<220> FEATURE:
<223> OTHER INFORMATION: primer

<400> SEQUENCE: 6
cacgaactcc agcaggacca tg                                              22

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
tgtaggtact aacactggct cgtgtgacaa                                      30

<210> SEQ ID NO 8
<211> LENGTH: 30
<212> TYPE: DNA
<213> ORGANISM: Artificial
<220> FEATURE:
<223> OTHER INFORMATION: primer

<400> SEQUENCE: 8
gggtgttgaa ggtctcaaac atgatctgta                                      30

<210> SEQ ID NO 9
<211> LENGTH: 25
<212> TYPE: DNA
<213> ORGANISM: Artificial
<220> FEATURE:
<223> OTHER INFORMATION: primer

<400> SEQUENCE: 9
caaggacgac ggcaactaca agacc                                           25

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
gctcgtccat gccgagagtg a                                               21

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
tcgagctgaa gggcatcgac                                                 20

<210> SEQ ID NO 12
<211> LENGTH: 22
<212> TYPE: DNA
<213> ORGANISM: Artificial
<220> FEATURE:
<223> OTHER INFORMATION: primer
```

<400> SEQUENCE: 12
tcacgaactc cagcaggacc at                                           22

<210> SEQ ID NO 13
<211> LENGTH: 19
<212> TYPE: DNA
<213> ORGANISM: Artificial
<220> FEATURE:
<223> OTHER INFORMATION: primer

<400> SEQUENCE: 13
tggacttcga gcaggagat                                               19

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
cctgcttgct gatccacatg                                              20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
gagccaccaa tccacactga                                              20

<210> SEQ ID NO 16
<211> LENGTH: 1096
<212> TYPE: DNA
<213> ORGANISM: Homo sapiens
<220> FEATURE:
<221> NAME/KEY: CDS
<222> LOCATION: (14)..(352)

<400> SEQUENCE: 16

```
gaattcatta gcc atg gat gta ttc atg aaa gga ctt tca aag gcc aag          49
            Met Asp Val Phe Met Lys Gly Leu Ser Lys Ala Lys
              1               5                  10 gag gga gtt gtg gct gct gct gag aaa acc aaa cag ggt gtg gca gaa         97
Glu Gly Val Val Ala Ala Ala Glu Lys Thr Lys Gln Gly Val Ala Glu
         15                  20                  25 gca gca gga aag aca aaa gag ggt gtt ctc tat gta ggc tcc aaa acc        145
Ala Ala Gly Lys Thr Lys Glu Gly Val Leu Tyr Val Gly Ser Lys Thr
 30                  35                  40 aag gag gga gtg gtg cat ggt gtg gca aca gtg gct gag aag acc aaa        193
Lys Glu Gly Val Val His Gly Val Ala Thr Val Ala Glu Lys Thr Lys
 45                  50                  55                  60 gag caa gtg aca aat gtt gga gga gca gtg gtg acg ggt gtg aca gca        241
Glu Gln Val Thr Asn Val Gly Gly Ala Val Val Thr Gly Val Thr Ala
                 65                  70                  75 gta gcc cag aag aca gtg gag gga gca ggg agc att gca gca gcc act        289
Val Ala Gln Lys Thr Val Glu Gly Ala Gly Ser Ile Ala Ala Ala Thr
             80                  85                  90 ggc ttt gtc aaa aag gac cag ttg ggc aag gaa ggg tat caa gac tac        337
Gly Phe Val Lys Lys Asp Gln Leu Gly Lys Glu Gly Tyr Gln Asp Tyr
         95                 100                 105
```

```
gaa cct gaa gcc taa gaaatatctt tgctcccagt ttcttgagat ctgctgacag    392
Glu Pro Glu Ala
    110 atgttccatc ctgtacaagt gctcagttcc aatgtgccca gtcatgacat ttctcaaagt    452 ttttacagtg tatctcgaag tcttccatca gcagtgattg aagtatctgt acctgccccc    512 actcagcatt tcggtgcttc cctttcactg aagtgaatac atggtagcag gtctttgtg    572 tgctgtggat tttgtggctt caatctacga tgttaaaaca aattaaaaac acctaagtga    632 ctaccactta tttctaaatc ctcactattt ttttgttgct gttgttcaga agttgttagt    692 gatttgctat catatattat aagattttta ggtgtctttt aatgatactg tctaagaata    752 atgacgtatt gtgaaatttg ttaatatata taatacttaa aaatatgtga gcatgaaact    812 atgcacctat aaatactaaa tatgaaattt taccattttg cgatgtgttt tattcacttg    872 tgtttgtata taaatggtga gaattaaaat aaaacgttat ctcattgcaa aaatatttta    932 tttttatccc atctcacttt aataataaaa atcatgctta taagcaacat gaattaagaa    992 ctgacacaaa ggacaaaaat ataaagttat taatagccat ttgaagaagg aggaattta    1052 gaagaggtag agaaaatgga acattaaccc tacactcgga attc                    1096

<210> SEQ ID NO 17
<211> LENGTH: 112
<212> TYPE: PRT
<213> ORGANISM: Homo sapiens

<400> SEQUENCE: 17

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Glu Gly Tyr Gln Asp Tyr Glu Pro Glu Ala
            100                 105                 110

<210> SEQ ID NO 18
<211> LENGTH: 112
<212> TYPE: PRT
<213> ORGANISM: Homo sapiens

<400> SEQUENCE: 18

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Pro Gly Lys
            20                  25                  30

Thr Lys Glu Gly Val Leu Tyr Val Gly Ser Lys Thr Lys Glu Gly Val
        35                  40                  45

Val His Gly Val Thr Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80
```

```
Thr Val Glu Gly Ala Gly Ser Ile Ala Ala Ala Thr Gly Phe Val Lys
            85                  90                  95

Lys Asp Gln Leu Gly Lys Glu Gly Tyr Gln Asp Tyr Glu Pro Glu Ala
            100                 105                 110

<210> SEQ ID NO 19
<211> LENGTH: 1096
<212> TYPE: DNA
<213> ORGANISM: Homosapiens

<400> SEQUENCE: 19
gaattcatta gccatggatg tattcatgaa aggactttca aaggccaagg agggagttgt      60
ggctgctgct gagaaaacca aacagggtgt ggcagaagca cccgggaaga caaaagaggg     120
tgttctctat gtaggctcca aaaccaagga gggagtggta catggtgtga caacagtggc     180
tgagaagacc aaagagcaag tgacaaatgt tggaggagca gtggtgacgg tgtgacagc      240 agtagcccag aagacagtgg agggagcagg gagcattgca gcagccactg gctttgtcaa     300
aaaggaccag ttgggcaagg aagggtatca agactacgaa cctgaagcct aagaaatatc     360
tttgctccca gtttcttgag atctgctgac agatgttcca tcctgtacaa gtgctcagtt     420
ccaatgtgcc cagtcatgac atttctcaaa gtttttacag tgtatctcga agtcttccat     480
cagcagtgat tgaagtatct gtacctgccc ccactcagca tttcggtgct tcccttttcac    540 tgaagtgaat acatggtagc agggtctttg tgtgctgtgg attttgtggc ttcaatctac     600
gatgttaaaa caaattaaaa acacctaagt gactaccact tatttctaaa tcctcactat     660 tttttgttg ctgttgttca gaagttgtta gtgatttgct atcatatatt ataagatttt      720
taggtgtctt ttaatgatac tgtctaagaa taatgacgta ttgtgaaatt tgttaatata     780
tataatactt aaaaatatgt gagcatgaaa ctatgcacct ataaatacta aatatgaaat     840
tttaccattt tgcgatgtgt tttattcact tgtgtttgta tataaatggt gagaattaaa     900
ataaaacgtt atctcattgc aaaaatattt tattttttatc ccatctcact ttaataataa   960
aaatcatgct tataagcaac atgaattaag aactgacaca aaggacaaaa atataaagtt    1020
attaatagcc atttgaagaa ggaggaattt tagaagaggt agagaaaatg gaacattaac    1080
cctacactcg gaattc                                                   1096
```

METHODS FOR INTRODUCING A HUMAN GENE INTO A MARMOSET EMBRYO FOR MAKING A TRANSGENIC MARMOSET

The present application is a 35 U.S.C. §371 National Stage patent application of International patent application PCT/JP2008/072732, filed on Dec. 9, 2008, which claims priority to Japanese patent application JP 2008-017955, filed on Jan. 29, 2008.

TECHNICAL FIELD

The present invention relates to production of a transgenic non-human primate animal that can be used as a human disease model animal and relates to a method for introducing a gene(s) into an early embryo of a primate animal.

BACKGROUND ART

Various human disease model animals have been produced using mice or rats. By genetic manipulation, such as introduction of a gene involved in a human disease into a non-human animal, knocking out of a gene homologous to a gene involved in a human disease, or the like, a transgenic non-human animal is produced. The transgenic non-human animal can be used as a human disease model animal. However, it is difficult to estimate the propriety of clinical application to humans based on the results obtained using these animals, as there are anatomical, physiological, and genetic differences between mice or rats and humans. Hence, the use of primates evolutionarily closely related to humans as transgenic animals has been desired.

Production of a transgenic non-human animal requires introduction of a foreign gene(s) such as a gene involved in a human disease into an early embryo of a non-human animal. Conventional methods therefor are DNA microinjection, a method using a virus such as a lentivirus as a vector, and the like. However, microinjection is problematic in that embryonic damage is significant and in lowering gene transfer efficiency (see Hammer, R. E. et al. Nature 315, 680-3 (1985)). It has been necessary to use many oocytes to compensate for such inefficiency. However, it has been difficult to prepare many oocytes in the cases of primates, domestic animals, or the like because of ethical and economical reasons. Accordingly, methods using retroviral vectors have been conducted for livestock (see Chan, A. W. et al., Proc Natl Acad Sci U.S.A. 95, 14028-33 (1998); Hofmann, A. et al. EMBO Rep 4, 1054-60 (2003); and Hofmann, A. et al. Biol Reprod 71, 405-9 (2004)). Such methods using retroviral vectors are problematic in that introduced transgenes are suppressed in the animal body (see Chan, A. W. et al., Science 291, 309-12 (2001)). To remedy such problems of gene suppression, lentiviral vectors have been used for cattle and pigs (see Hofmann, A. et al. EMBO Rep 4, 1054-60 (2003); and Hofmann, A. et al. Biol Reprod 71, 405-9 (2004)).

Regarding primates, production of transgenic rhesus monkeys (*Macaca mulatta*) has been attempted using retroviruses and lentiviruses (see Chan, A. W. et al., Science 291, 309-12 (2001); and Wolfgang, M. J. et al. Proc Natl Acad Sci U.S.A. 98, 10728-32 (2001)). However, even in the case of using a lentivirus, transgene expression is observed in placenta, but it has never been observed in neonates (see Wolfgang, M. J. et al. Proc Natl Acad Sci U.S.A. 98, 10728-32 (2001)). Production of rhesus monkeys introduced a human Huntington gene has also been reported (see S. H. Yang et al., Nature, vol. 453, No. 7197, 921-??? (2008)), but neither transgene expression in surviving neonates nor germline transmission of the introduced transgene has been observed therein. Rhesus monkeys and crab-eating monkeys (*Macaca fascicularis*) have been conventionally used as experimental non-human primates. However, these monkeys are problematic in that it is difficult to obtain starter animals for the production of model animals because of the low reproductive rates of these primates, that it takes about 3 years to obtain next-generation animals, and that only about 10 animals per instance can be obtained as next-generation animals.

As described above, high efficiency of gene introduction into embryos has not been achieved with the use of certain mammals such as primates.

With the use of certain animals such as mice, transgenic animals can be produced using ES cells. However, transgenic primate animals wherein a foreign transgene is transmitted to the germline could have not been produced using ES cells. For example, the present inventors have succeeded in production of marmoset ES cells (see International Patent Publication WO2006/029093 Pamphlet), but failed to produce transgenic primates wherein germline transmission takes place via techniques using ES cells.

Meanwhile, a technique referred to as subzonal insemination has been used as an artificial insemination technique (see JP Patent Publication (Kokai) No. H10-185919 A (1998)). This technique accelerates fertilization by injecting spermatozoa into the perivitelline space, which is the space between the vitelline membrane and the zona pellucida. In such cases, oocytes have been treated with a sucrose solution in advance, so as to expand the perivitelline space, for example. This is a technique for artificially causing spermatozoa which have impaired ability for penetrating the clear zone to enter the egg. For artificial insemination, an object is to cause single spermatozoon to enter a single oocyte, but introduction of a large amount of DNA into one cell is not an object. It has not always been possible to achieve a high fertilization rate with this method. Subsequently, this has been replaced by intracytoplasmic sperm injection, which involves direct sperm injection into cytoplasm.

DISCLOSURE OF THE INVENTION

An object of the present invention is to provide a gene transfer method for introducing a gene into an early embryo to produce a human disease model animal using a non-human primate such as a marmoset.

The common marmoset (*Callithrix jacchus*) is a kind of very small New World monkey belonging to an anthropoid family closely related to humans. The common marmosets have advantages over large monkeys in that their reproductive efficiency is high and they can be easily handled because of their small size. The present inventors have considered that if it becomes possible to produce human disease (e.g., Parkinson's disease and Huntington's disease) model marmosets via foreign gene introduction or disruption of a target gene, such human disease model marmosets will significantly contribute to the development of regenerative medicine for nerves or other organs. The present inventors have previously succeeded in production of ES cells of the common marmoset (WO2006/029093) and then attempted but failed in the production of transgenic common marmosets using ES cells. Hence, the present inventors have attempted to produce transgenic common marmosets with other techniques, conducted basic research concerning developmental engineering and molecular biological techniques that are essential for production of transgenic common marmosets, and then intensively examined cell preparation methods or the like for efficient production of transgenic common marmosets.

Specifically, the present inventors have established a gene transfer method for introducing a gene into an early embryo of a common marmoset, which is an essential technique for production of transgenic common marmosets. In particular, it has been conventionally difficult to increase the efficiency of introducing a foreign gene into an early embryo of primates. Successful production of transgenic primates through introduction of a human gene has almost never been reported. The present inventors have discovered that a foreign gene can be efficiently introduced into an early embryo through the use of a solution containing sucrose upon introduction of a foreign gene into an early embryo using a viral vector. Thus, the present inventors have completed the present invention.

The present invention encompasses the following [1] to [17].

[1] A method for introducing a foreign gene into an early embryo of a non-human primate animal, comprising adding an early embryo of a non-human primate animal to a 0.2 M-0.3 M sucrose solution to perform sucrose treatment, increasing the volume of the perivitelline space, and then injecting a viral vector containing a human foreign gene operably linked to a promoter into the perivitelline space of the early embryo.

[2] The method according to [1], wherein the volume of the perivitelline space of the early embryo is increased by sucrose treatment to 1.2- to 8-fold the volume of the same before sucrose treatment.

[3] The method according to [1], wherein the foreign gene in an amount 1.2- to 8-fold the amount of the foreign gene that can be injected into an early embryo not treated with sucrose is injected into an early embryo.

[4] The method according to any one of [1] to [3], wherein the primate animal is a marmoset.

[5] The method according to any one of [1] to [4], wherein the viral vector is selected from the group consisting of a lentiviral vector, an adenoviral vector, and an adeno-associated viral vector.

[6] The method according to [5], wherein the viral vector is a lentiviral vector.

[7] The method according to any one of [1] to [6], wherein the early embryo is a preimplantation embryo between the pronuclear stage and the morula stage that is obtained by natural mating.

[8] The method according to any one of [1] to [6], wherein the early embryo is an embryo between the pronuclear stage and the morula stage that is obtained by artificial insemination.

[9] The method according to any one of [1] to [8], wherein the viral vector is injected at a titer ranging from $1.3 \times 10^3$ CFU to $1.3 \times 10^5$ CFU per embryo.

[10] A method for producing a transgenic non-human primate animal in which a foreign gene can be transmitted to the germline, which comprises introducing a foreign gene into an early embryo by the method according to any one of [1] to [9], implanting the early embryo containing the foreign gene introduced therein into a surrogate mother, and then developing the embryo.

[11] The method for producing a transgenic non-human primate animal according to [10], wherein the foreign gene is a gene involved in a human disease.

[12] The method for producing a transgenic non-human primate animal according to [11], wherein the gene involved in a human disease is a mutant α-synuclein gene that is a causative gene for human Parkinson's disease or a mutant Huntington gene that is a causative gene for human Huntington's disease and the human disease model primate animal is a human Parkinson's disease model primate animal or a human Huntington's disease model primate animal.

[13] The method for producing a transgenic non-human primate animal according to [11], wherein the foreign gene is used for knocking out an endogenous non-human primate animal orthologue gene of a human gene involved in a human disease and the transgenic non-human primate animal is a human disease model knock-out primate animal.

[14] A transgenic primate animal, which is produced by the method according to any one of [11] to [13], wherein a foreign transgene has germline transmission ability.

[15] A transgenic primate animal, wherein a mutant human α-synuclein gene that is a causative gene for human Parkinson's disease or a mutant human Huntington gene that is a causative gene for human Huntington's disease is introduced thereinto and the gene is transmitted to the germline.

[16] The transgenic primate animal according to [15], which is a human Parkinson's disease model primate animal or a human Huntington's disease model primate animal.

[17] The transgenic primate animal according to [15] or [16], wherein the primate animal is a marmoset.

This description hereby incorporates the entire content of the description and/or the drawings of Japanese Patent Application No. 2008-017955, which is the basis of the priority claim of this application.

BRIEF DESCRIPTION OF THE DRAWINGS

FIG. 15 shows the results of a parentage test using microsatellite markers.

BEST MODE FOR CARRYING OUT THE INVENTION

Figure 1:
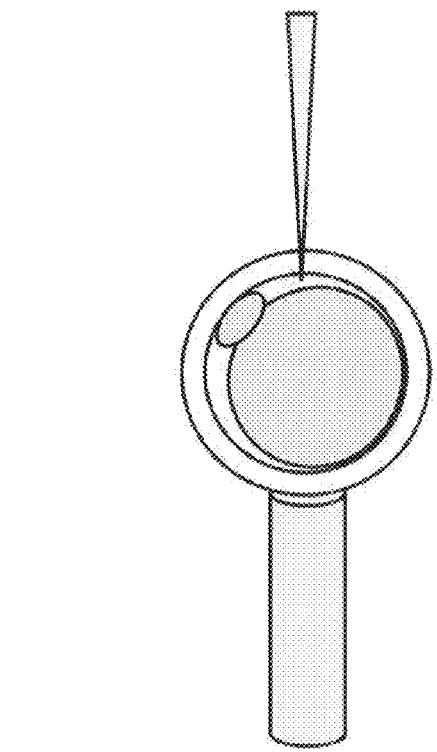
FIG. 1 is a schematic view showing the outline of a method for injecting a viral vector into a perivitelline space.
Figure 1:
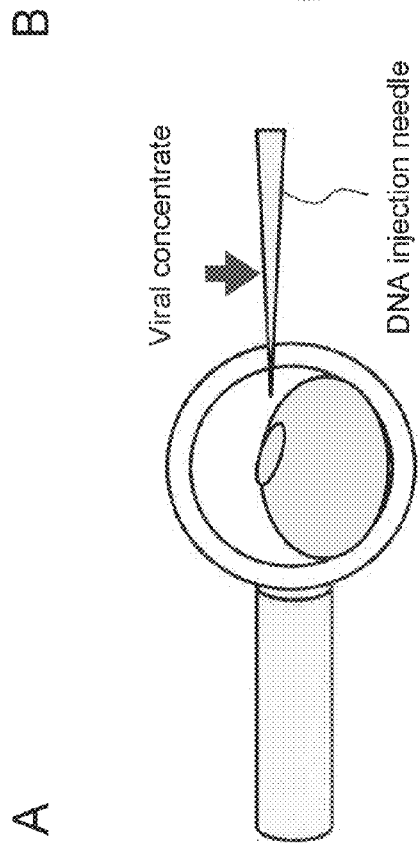

The present invention will be explained in detail as follows.

Marmosets such as the common marmoset (*Callithrix jacchus*), which is a kind of New World monkey, are very small anthropoid monkeys closely related to humans. Marmosets have higher reproductive efficiency than large monkeys and can be easily handled because of their small size. Moreover, marmosets have a short gestation period (about 144 days) and reach sexual maturity within 12-18 months. Female marmosets have 2 to 3 offspring per delivery and have 40 to 80 offspring throughout their life.

Human disease model animals, which are primate animals such as marmosets, can be obtained by: introducing an orthologue gene of a primate animal corresponding to a human gene involved in a human disease or a human gene involved in a human disease into a primate animal and then causing high-level expression of the protein of such causative gene; or knocking out such an orthologue gene of a primate animal or knocking in a human gene involved in a human disease.

Examples of such human disease include Parkinson's disease and Huntington's disease. Parkinson's disease model animals can be produced by introducing a mutant α-synuclein gene into primate animals. The nucleotide sequence of a human wild-type α-synuclein gene is shown in SEQ ID NO: 16 and the amino acid sequence of an α-Synuclein protein is shown in SEQ ID NO: 17. The mutant α-synuclein gene is a causative gene of human Parkinson's disease, in which the nucleotide sequence (gca) ranging from nucleotide 101 to 103 of SEQ ID NO: 16, which corresponds to alanine at position 30, is mutated to ccc, cct, cca, or ccg, so that alanine at position 30 of the α-Synuclein protein is mutated to proline. Also, such mutant α-synuclein gene is characterized in that the nucleotide sequence (gca) ranging from nucleotide 170 to 172 of SEQ ID NO: 16, which corresponds to alanine at position 53, is mutated to acu, acc, aca, or acg, so that alanine at position 53 of the α-Synuclein protein is mutated to threonine. In the present invention, a mutant gene, which has nucleotide mutations including substitution of alanine at position 30 of the α-synuclein protein with proline and substitution of alanine at position 53 of the same with threonine with respect to a human wild-type α-synuclein gene, is referred to as a mutant human α-synuclein gene causing Parkinson's disease. For example, in the nucleotide sequence shown in SEQ ID NO: 16, "g" at position 101 is mutated to "c" and "g" at position 170 is mutated to "a." Also, such mutant α-Synuclein protein comprises the amino acid sequence shown in SEQ ID NO: 17 in which alanine at position 30 is mutated to proline and alanine at position 53 is mutated to threonine (SEQ ID NO: 18). When a primate animal is a marmoset, whereas a nucleotide sequence ranging from nucleotide 170 to nucleotide 172 of the human wild-type α-synuclein gene is "gca" in the nucleotide sequence shown in SEQ ID NO: 16, the same of a marmoset wild-type α-synuclein gene is "aca." Amino acid at position 53 of the wild-type marmoset α-Synuclein protein is threonine, whereas the same of the wild-type human α-Synuclein protein is alanine. Therefore, the mutant human α-Synuclein protein is identical to a protein in which alanine at position 30 of a wild-type marmoset α-Synuclein protein is mutated to proline. An example of a mutant α-synuclein gene sequence that can be introduced into a human Parkinson's disease model marmoset is shown in SEQ ID NO: 19. In the nucleotide sequence of SEQ ID NO: 19, not only the nucleotide sequence ("gca" is mutated to "ccc") corresponding to alanine at position 30 of an α-Synuclein protein, but also the nucleotide sequence corresponding to glycine at position 31 is mutated with respect to a wild-type gene ("gga" is mutated to "ggg"). However, a mutation in the nucleotide sequence corresponding to glycine at position 31 causes no amino acid substitution. This mutation is due to the provision of a convenience for mutant gene selection. Specifically, the nucleotide sequence corresponding to amino acids 30 to 31 is cccggg, so that a new recognition sequence (the sequence not existing in the wild-type) for a restriction enzyme Sma I is produced. Upon mutant selection, clones that are digested by Sma I, in which a mutation of interest has been introduced, will be easily selected through selection of clones.

For example, human Parkinson's disease model primate animals presenting the symptoms of human Parkinson's disease can be obtained by introducing a DNA comprising the nucleotide sequence shown in SEQ ID NO: 19 or a DNA comprising a nucleotide sequence that has a deletion, a substitution, or an addition of one or several nucleotides with respect to the nucleotide sequence shown in SEQ ID NO: 19 into primate animals. Here, the term "one or several" refers to 1 to 5, preferably 1 to 4, and 1 to 3, further preferably 1 or 2, and particularly preferably 1. Furthermore, a DNA that can also be introduced herein has at least 95% or more, preferably 97% or more, further preferably 98% or more, and particularly preferably 99% or more identity with the nucleotide sequence shown in SEQ ID NO: 19 as calculated using BLAST (e.g., with the use of default; that is, initial set parameters) or the like; and can cause a primate animal to present the symptoms of human Parkinson's disease when introduced into the animal. Moreover, a DNA that can be introduced herein hybridizes under stringent conditions to the nucleotide sequence shown in SEQ ID NO: 19 and can cause a primate animal to present the symptoms of human Parkinson's disease when introduced into the animal. Here, the term "stringent conditions" refers to the conditions described in Sambrook et al., Molecular Cloning: A Laboratory Manual, 2 ed. Vol. 1, pp. 1. 101-104, Cold Spring Harbor Laboratory Press, (1989), for example. According to Sambrook et al., such conditions are overnight hybridization conditions of about 55° C., and 5×SSC using a pre-washing solution (5×SSC, 0.5% SDS, and 1.0 mM EDTA (pH 8.0)), for example. Also, hybridization that is performed at an even higher temperature and washing are also included in such conditions. At this time, the temperature and the salt concentration of a washing solution can be appropriately adjusted depending on various factors such as the lengths of probes. For example, conditions of 5×SSC or less and 20° C. or higher can be employed herein.

When a mutant human α-synuclein gene is introduced into a primate animal, anα-synuclein gene that is originally present in the primate animal and the mutant human α-synuclein gene coexist within the thus obtained transgenic primate animal. The expression product of the mutant human α-synuclein gene causes the development of the symptoms of human Parkinson's disease. In addition, at this time, an α-synuclein gene that is originally present in a primate animal can be substituted with a mutant human α-synuclein gene by homologous recombination or the like.

Also, a Huntington's disease model primate animal can be produced by introducing a mutant in which a repeating sequence of CAG sequence ranging from 37 to 876 is present in the 1$^{st}$ exon of a human huntington gene (HTT gene) into a primate animal.

Through introduction of a causative gene for such human disease into a primate animal, the transgenic primate animal will develop pathological conditions of the above human disease. For example, in the case of a Parkinson's disease model primate animal, it will develop symptoms such as tremor, akinesia, muscle rigidity, impairment of postural reflexes, and dopamine decreases in nerve cells within 1 to several years after birth. Also in the case of Huntington's disease, animals will develop symptoms such as shrunken basal ganglia, shrunken frontal lobes, symptoms of dementia, and symptoms of epilepsy. Depending on the disease, it can take time for the animal to develop such symptoms. In the present invention, a transgenic primate animal produced by introducing a causative gene, which is in a state of not yet presenting such symptoms, is also referred to as a disease model animal.

In the transgenic primate animal of the present invention, a transgene that is a foreign gene introduced therein is transmitted to the germline and then inherited to offspring via the germline. Specifically, the transgenic primate animal of the present invention has germline transmission ability, so that transgene expression is observed in its offspring and the offspring of human disease model primate animals can also be used as human disease model primate animals. Germline transmission can be confirmed by collecting germ cells (egg or sperm) from a primary transgenic primate animal, fertilizing thereof with germ cells collected from a normal primate animal, developing fertilized eggs, and then detecting the presence of the transgene, for example.

A transgenic primate animal is produced via the following steps. Therefore, it becomes possible to efficiently produce transgenic primate animals only when each of the following steps is optimized and the steps are performed in combination:
(a) a step of collecting and recovering fertilized eggs of a primate animal, or a step of collecting unfertilized eggs and performing in vitro fertilization thereof;
(b) a step of performing genetic manipulation via introduction of a foreign gene into early embryos;
(c) a step of preserving fertilized eggs or early embryos; and
(d) a step of implanting early embryos into female primate surrogate mothers to cause development thereof.

The order of the above steps is complicated and the steps (a) to (d) are not always performed in this order.

Hereinafter, these steps are separately described in detail. Marmosets belonging to primates are mainly used as examples in the following explanation. However, the methods of the present invention are applicable to mammals with the small volumes of perivitelline spaces of early embryos, such as other primates or cattle.

(1) Step of Collecting Unfertilized Eggs of Marmosets

Unfertilized eggs can be collected by stimulating the ovary of a marmoset. An example of a method for stimulating ovaries is a method that involves administering follicle stimulating hormone (FSH) to a sexually mature female marmoset and then administering chorionic gonadotropin (CG). As FSH and CG, marmoset FSH and CG can be used and FSH and CG of species belonging to other primates including humans can also be used. Also, natural hormones may also be used and recombinant hormones may also be used. In view of ease for obtainment, human recombinant FSH (hFSH) or CG (hCG) can be properly used. The concentration of FSH to be administered ranges from 100 IU/ml to 1000 IU/ml, preferably ranges from 100 IU/ml to 750 IU/ml, and further preferably ranges from 100 IU/ml to 500 IU/ml. The dose of FSH ranges from 10 IU/animal to 100 IU/animal. FSH is continuously administered for 6 to 15 days, preferably for 7 to 15 days, more preferably for 8 to 15 days, further more preferably for 9 to 15 days, even further more preferably for 10 to 15 days, and particularly preferably for 10 or 11 days. Regarding the route of administration, intramuscular administration is preferred.

After FSH is administered every day during the above period, CG is administered. The concentration of CG to be administered ranges from 100 IU/ml to 1000 IU/ml, preferably ranges from 100 IU/ml to 750 IU/ml, and further preferably ranges from 100 IU/ml to 500 IU/ml. The dose of CG ranges from 10 IU/animal to 100 IU/animal. After administration of FSH, CG is administered for 7 to 21 days, preferably for 10 to 15 days, and further preferably for 12 days. Regarding the route of administration, intramuscular administration is preferred.

At 15 to 30, preferably 20 to 25, further preferably 21 or 22 hours after CG administration, follicular oocytes are collected. Follicular oocytes can be collected by aspiration using surgical operation techniques, for example.

(2) In Vitro Maturation of Collected Unfertilized Eggs

Collected oocytes are cultured for several hours to several days and preferably overnight in medium appropriate for maturation of primate oocytes, so as to cause in vitro maturation (IVM). As medium to be used for in vitro maturation, Waymouth medium (Invitrogen), IVM medium (Medicult), or the like can be used. IVM medium is desirable in view of the embryonic development rate after in vitro fertilization. The thus obtained mature oocytes are fertilized with spermatozoa by in vitro fertilization. Fertilized eggs are cultured in ISM1 medium or ISM2 medium, so as to cause the eggs to develop into early embryos. Here, the term "early embryo" refers to an embryo between the pronuclear stage and the blastocyst stage. To produce a transgenic marmoset through introduction of a foreign gene, embryos between the pronuclear stage (the PN stage to the 2PN stage) and the morula stage are preferred.

(3) Preservation of Marmoset Early Embryos

The thus obtained marmoset early embryos are cryopreserved if necessary.

At this time, a phosphate buffer-based vitrification solution (containing only 10% (v/v) to 15% (v/v) propylene glycol as polyhydric alcohol) for mammalian early embryos or mammalian ES cells (JP Patent Publication (Kokai) No. 2007-105013 A) is preferably used. The vitrification solution is a phosphate buffer-based preservative solution. Examples of such preservative solution include PB10 prepared by adding propylene glycol to a modified phosphate buffer (PB 1) and PEPeS prepared by adding propylene glycol, ethylene glycol, Percoll (registered trademark), and sucrose to PB1. P10 is prepared by adding 5% (v/v) to 15% (v/v), preferably 10% (v/v) to 15% (v/v), and particularly preferably 10% (v/v) propylene glycol to PB1. Also, PEPeS is prepared by adding 5% (v/v) to 15% (v/v), preferably 10% (v/v) to 15% (v/v), and particularly preferably 10% (v/v) propylene glycol, 25% (v/v) to 35% (v/v), preferably 30% (v/v) ethylene glycol, 15% (v/v) to 25% (v/v), preferably 20% (v/v) Percoll (registered trademark), and 0.2 M to 0.5 M, and preferably 0.3 M sucrose to PB1. Marmoset early embryos are immersed in the P10 vitrification solution for 1 to 20 minutes, preferably 3 to 15 minutes, and further preferably 5 to 10 minutes. Immersion may be performed at room temperature (22° C. to 25° C.). Subsequently, embryos pre-treated by immersion are added with the P10 vitrification solution into a cryopreservation tube and then cooled for dozens of seconds to several minutes, preferably 30 seconds to 2 minutes, and further preferably 1 minute at 0° C. to 5° C., and preferably at 0° C. Subsequently, embryos in P10 are placed in a PEPeS vitrification solution and then frozen at a low temperature of −196° C. or lower. The thus cryopreserved early embryos are treated as follows. For example, a frozen tube containing frozen embryos is removed from liquid nitrogen and placed at room temperature for 10 seconds to 60 seconds, and preferably for about 30 seconds.

Then a solution for thawing in an amount 5 to 10 times the content in the tube, which is kept at room temperature, is then injected for thawing. Subsequently, embryos are washed with the solution for thawing. Such solution for thawing is not limited, and a solution prepared by adding 0.2 M to 0.5 M and preferably 0.3 M sucrose to the above BP1 can be used, for example.

(4) Transformation of Marmoset Early Embryos by Genetic Manipulation

Genetic manipulation is carried out by introducing a gene involved in a human disease into a marmoset early embryo or knocking out an orthologue gene of a human gene (involved in a human disease) in a marmoset. In the present invention, a marmoset into which a human gene has been introduced and a marmoset in which a gene has been knocked out are referred to as transgenic marmosets. Genes to be introduced or genes to be knocked out are determined depending on disease type. When a gene involved in a human disease is introduced, the gene may be substituted with an marmoset orthologue gene of the relevant gene by homologous recombination or the like.

Gene introduction and gene knockout can be carried out by known genetic engineering techniques.

A DNA to be introduced into a marmoset is ligated to a promoter that can be expressed in marmoset cells. Examples of such promoter that can be expressed include mammalian cell-derived promoters such as a CAG (chicken β-actin) promoter, a PGK (phosphoglycerate kinase) promoter, and an EF1α (elongation factor 1 cc) promoter and virus promoters such as a cytomegalovirus (CMV) promoter, a simian virus 40 (SV40) promoter, a retrovirus promoter, a polyomavirus promoter, and an adenovirus promoter. Among these promoters, a CAG promoter and a CMV promoter are preferred. Also, an enhancer that enhances gene expression can also be integrated. A gene to be introduced and a promoter are operably linked and then introduced into a vector. Any vector may be used herein as long as it can induce in vivo expression of a transgene in an animal. A vector in which a promoter is integrated in advance may also be used herein. As a vector, a viral vector such as a retroviral vector, an adenoviral vector, or an adeno-associated viral vector is preferred. Among vectors, a retroviral vector and particularly a lentiviral vector are preferred. An example of lentiviruses is human immunodeficiency virus (HIV). For example, a SIN vector (SIN $3^{rd}$ generation VSV-G pseudotype human immunodeficiency viral vector ($3^{rd}$ generation lentiviral vector) (Miyoshi, H. et al., J Virol 72, 8150-7 (1998)) can be appropriately used.

A viral vector may be injected into the perivitelline space of an early embryo or the blastocyst cavity of a blastocyst. As an early embryo, an embryo obtained by artificial insemination or a preimplantation embryo obtained via fertilization by natural mating may be used. A viral vector to be injected preferably has a high titer. For example, a vector with a titer ranging from $1.3 \times 10^3$ CFU to $1.3 \times 10^5$ CFU is desirably injected into each embryo. As an early embryo, an embryo between pronuclear stages (PN stage to 2PN stage) and the morula stage is preferred. At such time, injection is performed by placing an early embryo in 0.2 M to 0.3 M and preferably 0.25 M sucrose in order to cause temporary shrinkage of the cytoplasm. This causes the volume of the perivitelline space to expand, so that a larger amount of a viral solution is injected. As a result, many foreign genes are introduced into an early embryo, causing transformation to easily take place. When an early embryo of a primate animal is used, the volume of the perivitelline space is expanded about 1.2- to 10-fold, preferably about 1.2- to 8-fold, further preferably about 1.3- to 8-fold, and even further preferably about 1.5- to 8-fold, or about 1.2- to 6.5-fold and preferably 1.3- to 6.5- fold. As one example, the volume of the perivitelline space of a marmoset embryo at the pronuclear stage is about 31.5 µl, which can be increased by sucrose treatment to about 231 pl, which is about 7.3-fold the original volume. Specifically, in the method of the present invention, the volume of the perivitelline space of an early embryo of a primate animal is increased by sucrose treatment about 1.2- to 10-fold, preferably about 1.3- to 8-fold, further preferably about 1.5- to 8-fold, and even further preferably about 2- to 8-fold the volume of the perivitelline space not treated with sucrose. The increased volume of the perivitelline space ranges from 100 µl to 500 µl, preferably ranges from 150 µl to 400 µl, and further preferably ranges from 200 µl to 300 µl. As a result, when simultaneously constructed vectors containing foreign genes are used, the amounts of genes that can be introduced into an early embryo treated with sucrose are about 1.2- to 10-fold, preferably about 1.3- to 8-fold, further preferably about 1.5- to 8-fold, and even further preferably about 2- to 8-fold the amounts of genes that can be introduced into an early embryo not treated with sucrose. At such time, an excessively high sucrose concentration is toxic to the embryos. Sucrose is desirably used at a concentration of 0.3 M or lower.

When a gene is introduced into an early embryo of the present invention, a method for treating an early embryo with sucrose is applicable to mammals in which the perivitelline space is so small that a sufficient amount of a viral vector solution cannot be injected. Examples of mammals with such small perivitelline spaces of the embryos include mammals belonging to primates and cattle.

A knockout marmoset can be produced by a known method such as homologous recombination. Homologous recombination is an intracellular phenomenon, by which two DNA molecules undergo homologous recombination via the same nucleotide sequence. In homologous recombination, a transfer vector is constructed by linking a promoter and a foreign gene so that the sequence of a target gene site is divided at the center. The vector is introduced into an early embryo, and then recombination takes place between a gene of a cell and the same sequence portion on the transfer vector. The thus sandwiched promoter and foreign gene are integrated into the genome of the cell, the target gene is divided to lose its functions, and thus the gene is knocked out. Such transfer vector can be designed and constructed based on the nucleotide sequence information of a target gene. Homologous recombination of a gene to be disrupted is performed using the transfer vector. Such transfer vector can be constructed according to a method described in Ed., D. M. Glover et al., Ikunoshin Kato, Translation Supervisor, DNA cloning 4-mammalsian system-($2^{nd}$ Edition) TaKaR or the like. The above various viral vectors can be used herein. A lentiviral vector is preferred. Also, a target gene can be knocked out by homologous recombination using a method that uses recombinase and a recognition site of the recombinase. According to the method, a DNA, in which a target gene to be knocked out is flanked by the nucleotide sequences of the above recombinase recognition site, and a DNA, in which a promoter is ligated upstream of the above recombinase, are introduced into marmosets. When the recombinase is expressed, the target gene flanked by the recombinase recognition sites is excised to lose its functions. An example of such method is a method using a Cre-loxP system. The Cre-loxP system is described in Sauer, B. et al., Proc. Natl. Acad, Sci. U.S.A., 85: 5166-5170, 1988; Gu, H., et al., Cell, 73, 1155-1164, 1993, and the like. According to these descriptions, a marmoset early embryo can be produced by knocking out a target gene using the Cre-loxP system.

(5) Implantation of Genetically Manipulated Marmoset Early Embryo into Marmoset Surrogate Mother Implantation into a surrogate mother is performed by implantation into the uterus of a surrogate mother by a known method.

At such time, the sexual cycle (ovulation cycle) of a recipient marmoset, which is a surrogate mother, and that of a donor marmoset, which is a donor of embryos, are synchronized in advance. Sexual cycle synchronization can be performed by administering a sex hormone such as prostaglandin.

The present invention will be explained more specifically with reference to the following examples, but the present invention is not limited to these examples.

Example 1

Examination of Ovarian Stimulation Using Hormonal Agent

Ovarian stimulation of common marmosets was examined as a form of basic research concerning developmental engineering using marmosets.

A human recombinant follicle stimulating hormone (hFSH) was continuously administered intramuscularly at 50 IU/marmoset to sexually mature female marmosets for 5 days, 10 days, and 11 days. On day 12 after the start of hFSH administration, a human chorionic gonadotropin (hCG) was administered intramuscularly at 75 IU/marmoset. At 21 to 37 hours after hCG administration, follicular oocytes were aspirated by surgical techniques and then oocytes were cultured overnight under 5% $CO_2$ using Waymouth medium (Invitrogen). In vitro maturation (IVM) culture was performed for oocytes and then in vitro fertilization (IVF) was performed. Thus, ovarian stimulation was examined.

As a result, 5 days, 10 days, and 11 days of FSH administration resulted in the 9.0±5.7, 12.8±6.7, and 14.7±8.1 as the average numbers of oocytes collected, respectively. No statistically significant difference was observed. However, a tendency was observed that the longer the hFSH administration period, the higher the number of oocytes obtained. Also, the IVM rates were 30.2%, 84.5%, and 67.4%, respectively. The IVM rates of groups subjected to 10 and 11 days of hFSH administration were observed to be significantly ($p<0.01$) higher than that of a group subjected to 5 days of the same. Similar significant differences ($p<0.01$) were also observed in IVF rates (0%, 35%, and 40%).

Subsequently, the time for exposure of oocytes to human chorionic gonadotropin (hCG), which induces the initiation of oocyte maturation, was examined. Oocytes were collected at 21 to 22 hours, 23 to 25 hours, and 31 to 37 hours after hCG administration. The number of oocytes collected, IVM rate, and in vitro fertility were examined. As a result, the average numbers of oocytes collected were 20.4±12.8, 10.67±4.0, and 3.67±1.5, respectively. When oocytes were collected at 21 to 22 hours after hCG administration, the number of oocytes collected was significantly high ($P<0.01$). The IVM rates were 72%, 54.3%, and 100%, respectively. It was demonstrated that oocyte collection at 31 to 37 hours after hCG administration results in a significantly high ($P<0.05$) IVM rate. Also, in vitro fertilization rates were 36.3%, 22.8%, and 76.7%, respectively.

It was revealed based on the above results that an appropriate duration of hFSH administration is 10 days or 11 days when a balance among the number of oocytes collected, oocyte maturation rate, and in vitro maturation rate is taken into consideration and the proper time for exposure to hCG ranges from 21 to 22 hours.

Example 2

Examination of In Vitro Fertilization

In vitro fertilization requires the steps of follicular oocyte collection, in vitro oocyte maturation, and in vitro fertilization. Hence, in vitro maturation medium was examined as the first stage of the examination of an in vitro fertilization method. Waymouth medium, which has been reported to be appropriate for monkey oocyte maturation, was compared with IVM medium (Medicult), which is used for human fertility treatment. As a result, the oocyte maturation rate (39.7%) in IVM medium was significantly lower than the maturation rate (61.5%) in Waymouth medium, but the rate of development to blastocysts (22.2%) after in vitro fertilization of oocytes that had matured in IVM medium was significantly higher than that in the case of maturation in Waymouth medium (4.3%).

The above results revealed that it would be better to cause maturation of embryos to be subjected to in vitro fertilization in IVM medium and then to implant them into uteri.

Example 3

Examination of Conditions for Implantation of Common Marmoset Early Embryo into Surrogate Uterus Fertilized eggs (257) obtained by in vitro fertilization and 49 fertilized eggs obtained by fertilization via natural mating were implanted into uteri and uterine tubes. These fertilized eggs were examined for developmental potency and an implantation method therefor. As a result of implantation of fertilized eggs obtained by in vitro fertilization, 3 offspring were obtained and the birth rate was 1.2%. On the other hand, in the case of implantation of fertilized eggs obtained via natural mating, 9 offspring were obtained and the birth rate was 18.4%. The birth rate in the case of eggs obtained via natural mating was significantly high ($P<0.01$). Furthermore, implantation sites of fertilized eggs including uterine tubes (n=140) and uteri (n=166) were compared in terms of birth rate. As a result, the birth rate in the case of implantation into uterine tubes was found to be 2.1% and the birth rate in the case of implantation into the uteri was found to be 5.4%. No significant difference in birth rate depending on implantation sites was observed.

Example 4

Examination of Cryopreservation of Common Marmoset Gamete and Early Embryo

Preservation of common marmoset early embryos has not yet been sufficiently examined. Hence, preservation of the early embryos between the morula stage and the blastocyst stage was examined. These common marmoset embryos (n=6) were preserved using a vitrification solution (developed by the present inventors; JP Patent Publication (Kokai) No. 2007-105013 A). The embryos were preserved for 12 to 20 days in liquid nitrogen and then warmed using a warming solution. As a result, all embryos were confirmed to develop into expanded blastocysts. It was revealed from the result that this method is also applicable to common marmoset early embryos.

Example 5

Examination of Injection of Lentiviral Vector Solution

PN (pronuclear) embryos were placed in 0.25 M sucrose or M2 medium containing no sucrose. Then, a lentiviral vector into which EGFP had been introduced was injected into the perivitelline spaces. In the case of embryos at the blastocyst stage, the virus was injected into blastocoels. Injection into embryos was performed using a DNA injection needle. A CAG promoter, a CMV promoter, a PGK promoter, or an EF1α promoter was used.

FIG. 1 shows an outline of a method for introducing a lentiviral vector into a perivitelline space.

Figure 2:
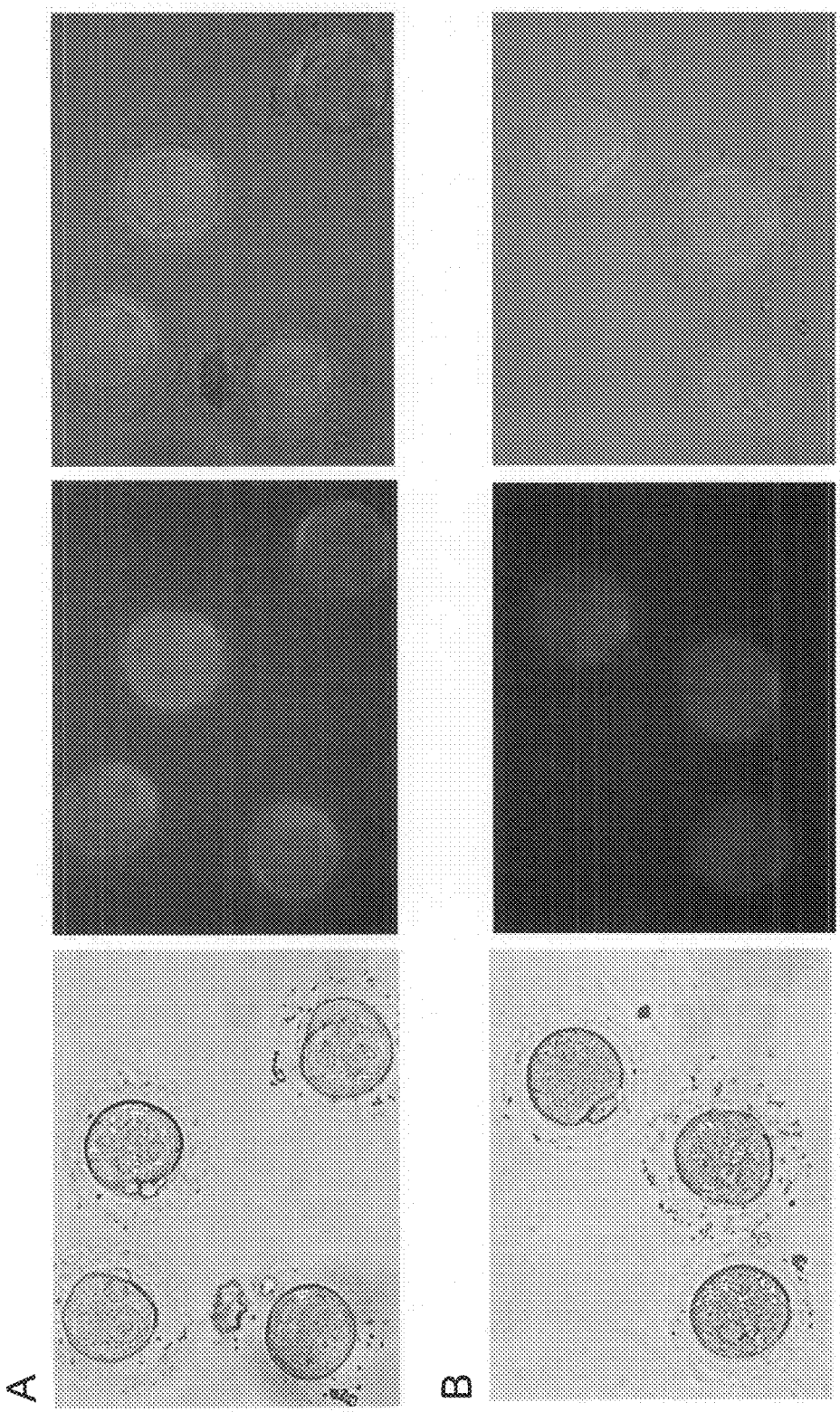
FIG. 2 shows photos showing embryos immediately after injection of a viral vector solution in a 0.25 M sucrose solution or M2 medium.

FIG. 2 shows photos of PN embryos immediately after injection of a lentiviral vector solution. FIG. 2A shows embryos for which a 0.25 M sucrose solution was used. FIG. 2B shows embryos for which M2 medium was used. As shown in FIG. 2, the viral solution was observed throughout the perivitelline spaces of PN embryos, for which the injection of the lentiviral vector solution had been performed in a sucrose solution. In contrast, the lentiviral vector was observed only in the periphery of the injection parts of PN embryos, for which injection of the lentiviral vector had been performed in M2 medium.

Figure 3:
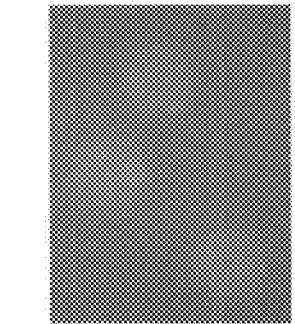
FIG. 3 shows photos showing embryos on days 2.5, 3.5, and 8.5 after injection of a viral vector solution in a 0.25 M sucrose solution or M2 medium.
Figure 3:
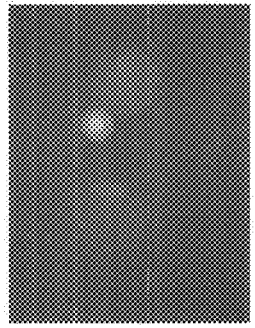
Figure 3:
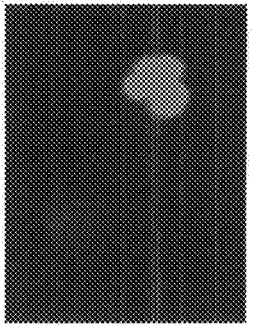
Figure 3:
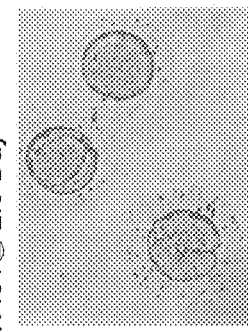
Figure 3:
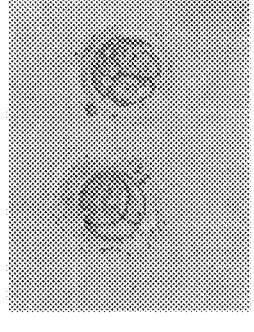
Figure 3:
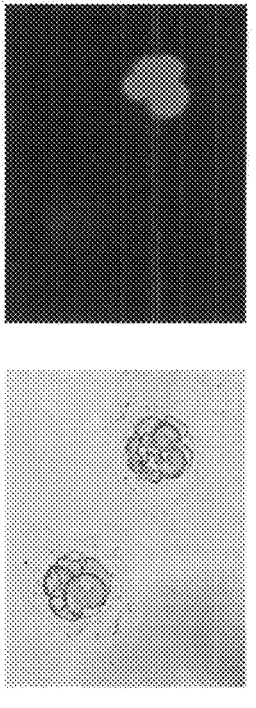
Figure 3:
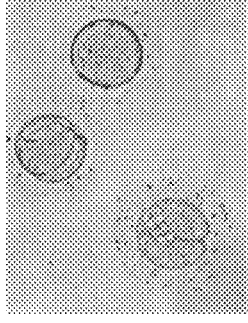
Figure 3:
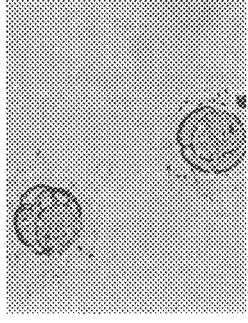
Figure 3:
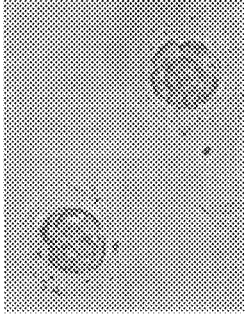

FIG. 3 shows photos of PN embryos on days 2.5, 3.5, and 8.5 after injection of a lentiviral solution. FIG. 3A shows PN embryos for which a 0.25 M sucrose solution was used and FIG. 3B shows PN embryos for which M2 medium was used.

Table 1 shows the gene expression rate of a case in which sucrose was used and the same of a case in which no sucrose was used. As shown in Table 1, GFP expression efficiency was significantly high in the case in which sucrose was used.

TABLE 1

|  | Suc+ | Suc− |
| --- | --- | --- |
| Lentivirus-injected egg | 44 | 76 |
| GFP-expressing egg | 43 | 31 |
| GFP expression rate | 97.7 | 40.8 |

When the sucrose concentration was excessively high, toxicity to embryos was observed.

Example 6

Gene Transfer into Common Marmoset Early Embryo

A. Method
(1) Unfertilized Egg Collection by Ovarian Stimulation Using Hormonal Agent Two-year-old or older marmosets were used.

A human recombinant follicle stimulating hormone (hFSH) was intramuscularly administered continuously at 50 IU/animal to sexually mature female marmosets for 11 days. At 12 days after the start of hFSH administration, a human chorionic gonadotropin (hCG) was intramuscularly administered at 75 IU/animal. At 21 to 37 hours after hCG administration, follicular oocytes were aspirated by surgical techniques using a 2.9-ml syringe and a 23-gauge injection needle. Follicular oocytes were aspirated in Waymouth medium containing 10% FBS. Oocytes were collected from medium, washed twice, and then cultured for 24 hours under conditions of 5% $CO_2$ and 38° C. using Waymouth medium. Only mature oocytes (metaphase II) were collected after culture and then used for in vitro fertilization (IV).

(2) Semen Collection and Preparation of Spermatozoa

Marmoset semen was collected using a Ferti Care personel vibrator (Kuederling, I. et al., Am J Primatol 52, 149-54 (2000)). Semen was collected in TYH medium and then washed twice with 3 ml of TYH medium. TYH medium (300 μl) was added and then left to stand in a $CO_2$ incubator at 30° C. for 10 minutes, so as to cause spermatozoa to swim.

(3) In Vitro Fertilization (IVF)

Oocytes treated with hyaluronidase were washed with TYH medium and then 70 μl thereof was dispensed in the form of droplets. The 70 μl of droplets contained a maximum of 10 oocytes. Spermatozoa (10 μl) prepared by the above method were added to the droplets. The final sperm concentration at this time was $5 \times 10^9$ spermatozoa/ml. At 26 to 30 hours after addition of spermatozoa, oocytes were collected and then washed with ISM1 medium (Medicult). Fertilized eggs were cultured in ISM1 medium for 48 hours, transferred into IISM2 medium containing feeder cells of mouse fetuses, and then cultured.

(4) Embryo Collection and Embryo Implantation

Cloprostenol (Estrumate, Takeda Schering-Plough K.K.), which is a prostaglandin F2α analog, was administered to donor and recipient common marmosets at 0.75 mg/animal on day 10 after the luteal phase, so that the ovulation cycles were synchronized (Summers, P. M. et al., J Reprod Fertil 73, 133-8 (1985)). A blood plasma sample (0.1 ml) was collected via the femoral vein on days 2, 9, 11, and 13 after cloprostenol administration. Ovulation dates were determined based on measurement of blood plasma progesterone levels using RIA. The date on which the blood plasma progesterone level reached 10 ng/ml was determined to be the ovulation date (day 0). On days 7 to 10 after the ovulation date, a donor marmoset was anaesthesized and eggs were collected from the common marmoset. The uterine cervix and both uterine tubes were exteriorized by paramedian laparotomy and then clamped. Uterine lumen ranging from an end (adjacent to the uterus) to the uterine cervix was flushed with 2.5 ml of DMEM (Dalbecco's-modified Eagle's medium) containing 10% FBS (fetal bovine serum). The medium used for flushing was collected from the uterine bottom using a 23-gauge injection needle placed on the uterine lumen. On day 4 after embryo collection, cloprostenol was further administered. Blood plasma progesteron concentration was determined using a DPC progesterone kit (Diagnostic Products Corp.).

Recipient common marmosets with ovulation cycles synchronized with that of the donor were anaesthesized and then the uteri and ovaries were exteriorized by paramedian laparotomy. A 23-gauge injection needle was inserted from the uterine cervix to an end (adjacent to the uterus) via the uterine lumen. One (1) to 3 embryos were implanted into the uterine lumen using a glass capillary pipette. After embryo implantation, each recipient was examined for the presence or the absence of pregnancy through measurement of the blood plasma progesterone level once a week until it became possible to monitor pregnancy through uterine palpation via the abdominal portion.

(5) Preparation and Introduction of Lentiviral Vector

Human embryonic kidney 293T cells were grown in DMEM supplemented with 10% heat-inactivated fetal calf serum, 100 units/ml penicillin, 100 μg/ml streptomycin, and 250 ng/ml amphotericin B. An SIN vector system was used for introduction of foreign DNA into CMES. Three types of vector expressing EGFP (Enhanced Green Fluorescence Protein) having 4 different promoters (CAG, CMV, EF-1, and PGK promoters) were constructed. The vectors were designated CAG-EGFP, CMV-EGFP, EF1α-EGFP, and PGK-EGFP, respectively.

A lentiviral vector was constructed by co-transfection of a vector and a packaging construct with VSV-G and Rev expression constructs into 293T cells using a Fugene 6 transfection reagent. On day 4 after transfection, viral particles contained in the medium were collected, filtered through a 0.22-μm filter, and then subjected to 4 hours of centrifugation at 25,000 rpm and 4° C. The viral precipitate was suspended with an original lentiviral vector supernatant with 1/1000 the volume of the viral precipitate in ISM2 medium (Medicult).

A lentivirus was introduced by injection of a viral solution into common marmoset embryos. 2PN (2 pronuclear)-to-morula embryos were placed in 0.25 M sucrose and then the virus was injected into the perivitelline spaces. In the case of embryos at the blastocyst stage, the virus was injected into blastocoels.

Injection into embryos was always carried out using a microinjector (Eppendorf femtojet express) and a micromanipulator (Narishige micromanipulator).

(6) RT-PCR

Poly A+ RNA was isolated from the hair roots, small skin sections, and erythrocytes using a Quick Prep Micro mRNA purification kit (GE health care). RNA samples were subjected to reverse transcription using an Improm-II Reverse Transcription system (Promega). Half of each Poly A+ RNA sample was reacted with reverse transcriptase for first strand cDNA synthesis and the remaining half thereof was reacted as a negative control sample without reverse transcriptase. Total RNAs were isolated from the placentae using an RNA II kit (MACHEREY-NAGEL). Total RNAs in amounts ranging from 100 ng to 1 μg were subjected to reverse transcription.

PCR was carried out using a 1/40-3/20 cDNA synthesis reaction mixture as a template. Ten (10)μl of a PCR mixture contained 1×PCR buffer (10 mM Tris-HCl (pH 9.0), 1.5 mM $MgCl_2$, and 50 mM KCl), 0.2 mM dNTPs, 0.2 μM primers, and 1.0 U of Taq polymerase. For detection of EGFP gene expression, PCR was performed for 35 cycles each consisting of denaturation at 94° C. for 30 seconds, annealing at 62° C. for 30 seconds, and extension at 72° C. for 30 seconds. Primer sequences used herein are as shown below.

```
                                            (SEQ ID NO: 1)
5'-GCACAAGCTGGAGTACAACTACAACAGC-3'
(EGFP5-5, forward primer)

(SEQ ID NO: 2)
5'-TCACGAACTCCAGCAGGACCAT-3'
(EGFP 3-1, reverse primer)
```

For detection of β-actin expression, PCR was performed for 30 cycles each consisting of denaturation at 94° C. for 30 seconds, annealing at 58° C. for 30 seconds, and extension at 72° C. for 30 seconds. Primer sequences used herein are as shown below.

```
                                            (SEQ ID NO: 3)
5'-TCCTGACCCTGAAGTACCCC-3'
(β-actin 001, forward primer)

(SEQ ID NO: 4)
5'-GTGGTGGTTGAAGCTGTAGCC-3'
(β-actin 002, reverse primer)
```

(7) Immunohistochemical Analysis

Tissues were embedded in OCT Compound, frozen in liquid nitrogen, and then stored at −80° C. until analysis. Five (5)-μm sections were prepared from the mass and then fixed using 4% paraformaldehyde at 4° C. for 30 minutes. Endogenous peroxidase activity was suppressed by 30 minutes of treatment at room temperature using 0.03% hydrogen peroxide solution. Sections were washed with water for 5 minutes and then washed with PBS for 2 minutes. Slides were subjected to blocking treatment at room temperature using 10% goat serum (Nichirei Corporation) for 10 minutes, followed by overnight reaction with rabbit anti-P.v antibody at 4° C. After 3 instances of washing with PBS, slides were reacted with a biotinylated secondary antibody and Simple Stain Mouse MAX PO (Nichirei Corporation) at room temperature for 30 minutes, followed by 3 instances of washing with PBS. Localization of the thus bound monoclonal antibodies was detected using a DAB (3,3,-diaminobenzidine tetrahydrochloride) horseradish peroxidase complex. Subsequently, samples were stained with HE (hematoxylin and eosin) and then embedded.

(8) FACS analysis

Peripheral blood samples were subjected to centrifugation at 2000 rpm for 5 minutes, whole blood cells were collected and then washed with 1 ml of PBS. Whole blood cells were suspended in 0.13 M $NH_4Cl$ and then subjected to centrifugation at 2000 rpm for 5 minutes. The resultants were washed again with 1 ml of PBS. Precipitates were incubated with mouse IgG1 anti-marmoset CD45 and 6C9 antibodies on ice for 30 minutes. Samples were washed with PBS and then mixed with an APC-labeled anti-mouse IgG antibody as a secondary antibody. The mixtures were incubated for 30 minutes on ice. After incubation with the secondary antibody, samples were washed with PBS and then suspended in 200 μl of a PI solution. FACS analysis was then performed.

(9) Southern Blot Analysis

Genomic DNA was extracted from skin, whole blood cells, and placental fibroblasts using a DNeasy Blood and Tissue kit (Qiagen). The genomic DNA of an animal into which CAG-EGFP had been injected was digested with Bam H I. The genomic DNA of an animal into which CMV-EGFP had been injected was digested with EcoR I. Southern blot analysis was carried out using a DIG system product (Roche). Specifically, 5 μg of genomic DNA was subjected to overnight eletrophoresis with 25 volts on 0.8% agarose gel and then the resultant was transferred to a Hybond-N+nylon membrane. CMV-EGFP was digested with EcoR I and then labeled with DIG using a PCR DIG probe synthesis kit. The membrane was subjected to hybridization with a DIG-labeled probe in DIG Easy Hyb Granules (Roche). After the membrane was washed, probes that had hybridized were immersed in a blocking solution for 30 minutes, for reaction with an anti-DIG alkaline phosphatase conjugate. After the membrane was washed, detection was performed using a CSPD probe that had hybridized, and then the resultant was exposed to an X-ray film.

(10) Determination of Transgene in Placenta and Offspring

Small placental sections and ear skin samples of mature animals were collected and then subjected to proteinase K treatment. Genomic DNA was extracted using a Mag Extractor System MFX-9600 Magnia R Plus (Toyobo Co., Ltd.). Furthermore, genomic DNA was extracted from whole blood samples of mature animals and hair roots of neonates using a DNeasy Blood & Tissue kit (Qiagen) and a QIAmp DNA Micro kit (Qiagen), respectively.

EGFP transgene was detected using the following PCR primer set.

```
GFPF1:   CTGGTCGAGCTGGACGGCGACG              (SEQ ID NO: 5)

GFPR1:   CACGAACTCCAGCAGGACCATG              (SEQ ID NO: 6)
```

A β-actin gene that is an endogenous control gene was detected using the following PCR primer set.

```
                                             (SEQ ID NO: 7)
Comm-β-ActinF:  TGTAGGTACTAACACTGGCTCGTGTGACAA (SEQ ID NO: 8)
Comm-β-ActinR:  GGGTGTTGAAGGTCTCAAACATGATCTGTA
```

The gene transfer efficiency of EGFP was almost the same as that of β-actin. Hence, relative determination of the EGFP transgene was carried out by a comparative CT method using an ABI PRISM 7700 Sequence Detection System (Applera Corporation, Applied Biosystems) and the Master Mix of SYBR Premix Ex Taq™ (Perfect Real Time, Takara Bio Inc).
(11) Fluorescence In Situ Hybridization (FISH)

To detect transgene(s), fluorescence in situ hybridization was carried out. Peripheral blood samples were cultured for several days in RPMI1640 medium containing phytohemagglutinin, concanavalin A, lipopolysaccharide, and 2-mercaptoethanol. After several hours of culture with BrdU having a final concentration of 30 μg/ml, colcemide having a final concentration of 0.02 μg/ml was added to the medium, and then samples were further cultured for several hours. Lymphocytes were collected and then treated with a hypotonic solution. Erythrocytes were removed and then precipitates were fixed using methanol/acetic acid (3:1 vol/vol). After fixation, cells were spread over a slide, air-dried overnight, stained using Hoechst33258, and then subjected to ultraviolet treatment.

CAG-EGFP was labeled with digoxigenin-11-dUTP and then hybridized as a probe at 37° C. overnight. Slides were washed under stringent conditions and then bound labels were detected using anti-Dig-Cy3. Leica CW4000 FISH and Leica CW4000 karyo were used for chromosome analysis.

B. Results (1) Production of Transgenic Common Marmoset Using Lentiviral Vector

As embryos for gene transfer, both in vitro fertilization (IVF) embryos and preimplantation embryos obtained by natural mating were used. An EGFP gene was introduced using 3 types of SIN vector containing 3 types of promoter (CAG, CMV, and EF1-α promoters). The vectors were designated CAG-EGFP, CMV-EGFP, and EF1α-EGFP, respectively. The thus constructed SIN vectors were injected into the perivitelline spaces of embryos. The perivitelline space of an early embryo of the common marmoset is so small that a sufficient amount of a viral solution cannot be injected. Even if a virus is injected into such small space, the resulting transgene expression rate is as low as 46%. Accordingly, a method was attempted that involved placing an early embryo in a 0.25 M sucrose solution to cause temporary shrinkage of the cytoplasm and thus to increase the amount of a viral solution to be injected. Pronuclear-to-morula embryos were used herein. In the case of embryos at the blastula stage, the SIN vectors were injected into blastocoels.

A total of 27 in vitro fertilization (IVF) embryos and a total of 64 preimplantation embryos obtained by natural mating were injected using SIN vectors with high titers (5.6×10$^9$ CFU to 5.6×10$^{11}$ CFU (colony-forming units/ml)). Table 2 shows the results. Lentiviral vectors were injected using 0.25 M sucrose into 16 of the 27 IVF embryos and 47 of the 64 preimplantation embryos (Table 3). The volume of each perivitelline space was expanded 1.2- to 6.5-fold by 0.25 M sucrose treatment. In the cases of 11 of the IVF embryos and 15 of the preimplantation embryos, embryos at the blastula stage were used and the SIN vectors were injected into blastocoels without using 0.25 M sucrose. EGFP expression takes place at 48 hours after the injection of SIN vectors. Thus, 4 of the IVF embryos and 12 of the preimplantation embryos were implanted into recipient animals immediately after injection. Accordingly, EGFP expression at the embryo stage was not measured. The EGFP expression rate at 48 hours after injection of a lentiviral vector was 89.7% in preimplantation embryos treated with sucrose, but it was 92.9% in untreated embryos at the blastula stage. EGFP expression was observed by fluorescence microscopy in 48 preimplantation embryos and 17 IVF embryos. Sixty-one (61) preimplantation embryos and 19 IVF embryos were implanted in recipient animals whose ovulation cycles were synchronized with that of the donor. One (1) to 3 embryos were implanted per cycle in each recipient animal. The total number of surrogate mothers was 51. Seven (7) recipients of implanted IVF embryos or preimplantation embryos became pregnant. Three (3) marmosets among them aborted after 43, 62, and 82 days, respectively. On days 144 to 147, a total of 5 healthy offspring were born from the remaining 4 marmosets. Each of 3 marmosets had 1 offspring and the remaining 1 marmoset had twins. The thus born 5 offspring were 4 female marmosets and 1 male marmoset. Among the 5 born offspring, 3 offspring were derived from embryos in which CAG-EGFP had been injected and 2 offspring were derived from embryos in which CMV-EGFP had been injected (Table 4). Therefore, CAG or CMV is preferred as a promoter. Also, as shown in Table 3, the EGFP expression rate was 40.8% when preimplantation (IVF) embryos not treated with sucrose had been used; and the same was 97.7% when preimplantation (IVF) embryos treated with sucrose had been used. The EGFP expression rate was significantly high (P<0.01) when sucrose treatment had been performed.

TABLE 2

|  | IVF | Natural |
|---|---|---|
| Number of GV oocytes | 460 | No data |
| Number of MII oocytes | 201 | No data |
| Number of IVFs performed (including MI) | 272 | No data |
| Fertilization rate (%) | 121 (77.9%) | No data |
| Number of embryos | — | 64 |
| Number of lentiviral injections | 27 | 64 |
| Embryos for which GFP expression was confirmed | 23 | 50 |
| Embryos expressing GFP | 17 (73.9%) | 48 (96.0%) |
| Embryos implanted | 19 | 61 |
| Number of surrogates | 13 | 38 |
| Number of pregnancies | 1 | 6 |
| Number of deliveries | 1 | 3 |
| Births | 1 (5.2%) | 4 (6.55%) |
| Number of transgenic animals (Tg) | 1 | 4 |
| Production rate (Tg/injection) | 3.7 | 6.25 |
| Production rate (Tg/ET) | 5.26 | 6.56 |
| Production rate (Tg/birth) | 100 | 100 |

GV: Germinal vesicle
MI: Metaphase I
MII: Metaphase II

TABLE 3

| | Promoter | | | | | | | |
|---|---|---|---|---|---|---|---|---|
| | CAG | | | | CMV | | | |
| | IVF | | Nat | | IVF | | Nat | |
| | Suc+ | Suc− | Suc+ | Suc− | Suc+ | Suc− | Suc+ | Suc− |
| Number of embryos subjected to lentiviral injections | 11 | 7 | 28 | 2 | 5 | 0 | 4 | 2 |
| Number of embryos, for which GFP expression was confirmed | 11 | 4 | 24 | 2 | 5 | 0 | 4 | 2 |
| GFP expression (%) | 8 (72.7%) | 4 (57.1%) | 23 (82.1%) | 1 (50%) | 3 (60.0%) | 0 | 4 (100%) | 2 (100%) |
| Number of implanted embryos | 8 | 5 | 26 | 1 | 2 | 0 | 4 | 2 |
| Number of surrogates | 3 | 5 | 14 | 1 | 1 | 0 | 2 | 1 |
| Number of pregnant marmosets | 1 (33.3) | 0 (0) | 4 (28.6) | 0 (0) | 0 (0) | 0 (0) | 1 (50.0) | 0 (0) |
| Number of deliveries | 1 | 0 | 2 | 0 | 0 | 0 | 1 | 0 |
| Number of births | 1 | 0 | 2 | 0 | 0 | 0 | 2 | 0 |
| Number of transgenic animals | 1 | 0 | 2 | 0 | 0 | 0 | 2 | 0 |
| Production rate (Tg/injection) | 9.09% | 0 | 7.14% | 0 | 0 | 0 | 50.0% | 0 |

| | Promoter | | | | | | | |
|---|---|---|---|---|---|---|---|---|
| | EF1 | | | | Total | | | |
| | IVF | | Nat | | IVF | | Nat | |
| | Suc+ | Suc− | Suc+ | Suc− | Suc+ | Suc− | Suc+ | Suc− |
| Number of embryos subjected to lentiviral injections | 0 | 4 | 17 | 11 | 16 | 11 | 47 | 15 |
| Number of embryos, for which GFP expression was confirmed | 0 | 2 | 16 | 4 | 16 | 6 | 44 | 8 |
| GFP expression (%) | 0 | 2 (50.0%) | 16 (100%) | 4 (100%) | 11 (68.8%) | 6 (100%) | 43 (97.7%) | 7 (87.5%) |
| Number of implanted embryos | 0 | 4 | 17 | 11 | 10 | 9 | 47 | 14 |
| Number of surrogates | 0 | 4 | 12 | 7 | 4 | 9 | 29 | 9 |
| Number of pregnant marmosets | 0 (0) | 0 (0) | 1 (10.7) | 0 (0) | 1 (25.0) | 0 (0) | 6 (21.4) | 0 (0) |
| Number of deliveries | 0 | 0 | 0 | 0 | 1 | 0 | 3 | 0 |
| Number of births | 0 | 0 | 0 | 0 | 1 | 0 | 4 | 0 |
| Number of transgenic animals | 0 | 0 | 0 | 0 | 1 | 0 | 4 | 0 |
| Production rate (Tg/injection) | 0 | 0 | 0 | 0 | 6.25% | 0 | 8.51% | 0 |

IVF: In vitro fertilization
Nat: Natural mating

TABLE 4

| Animal No. | Name | Gender | Introduced vector |
|---|---|---|---|
| No. 584 | HISUI | Female | CAG-EGFP |
| No. 587 | WAKABA | Female | CAG-EGFP |
| No. 588 | BANKO | Female | CAG-EGFP |
| No. 594 | KEI | Female | CMV-EGFP |
| No. 666 | KOU | Male | CMV-EGFP |

No. 594 and No. 666 are twins.

(2) Transgene Integration

The integration, transcription, and expression of the transgene in the marmoset offspring were detected using placentae, body hair, skin, and blood. Since a marmoset usually eats its placenta after delivery, only three placentae, of animals No. 584, No. 588, and Nos. 594/666, could be collected. Common marmoset twins share the same placenta, and thus No. 594 and No. 666 shared the same placenta.

Transgene integration was firstly determined immediately after birth for placentae and hair roots and then secondly determined by real-time PCR using genomic DNA extracted 1 to 2 months after birth from skin and blood. Table 5 shows the results of real-time PCR in terms of EGFP transgene levels relative to the blood of non-transgenic common marmosets. Transgene integration was observed in animals No. 584 and No. 588, but was detected at extremely low level in Nos. 594/666. Transgene integration in body hair, ear sections, and blood was observed in animals No. 584, No. 587, No. 594, and No. 666.

Figure 4:
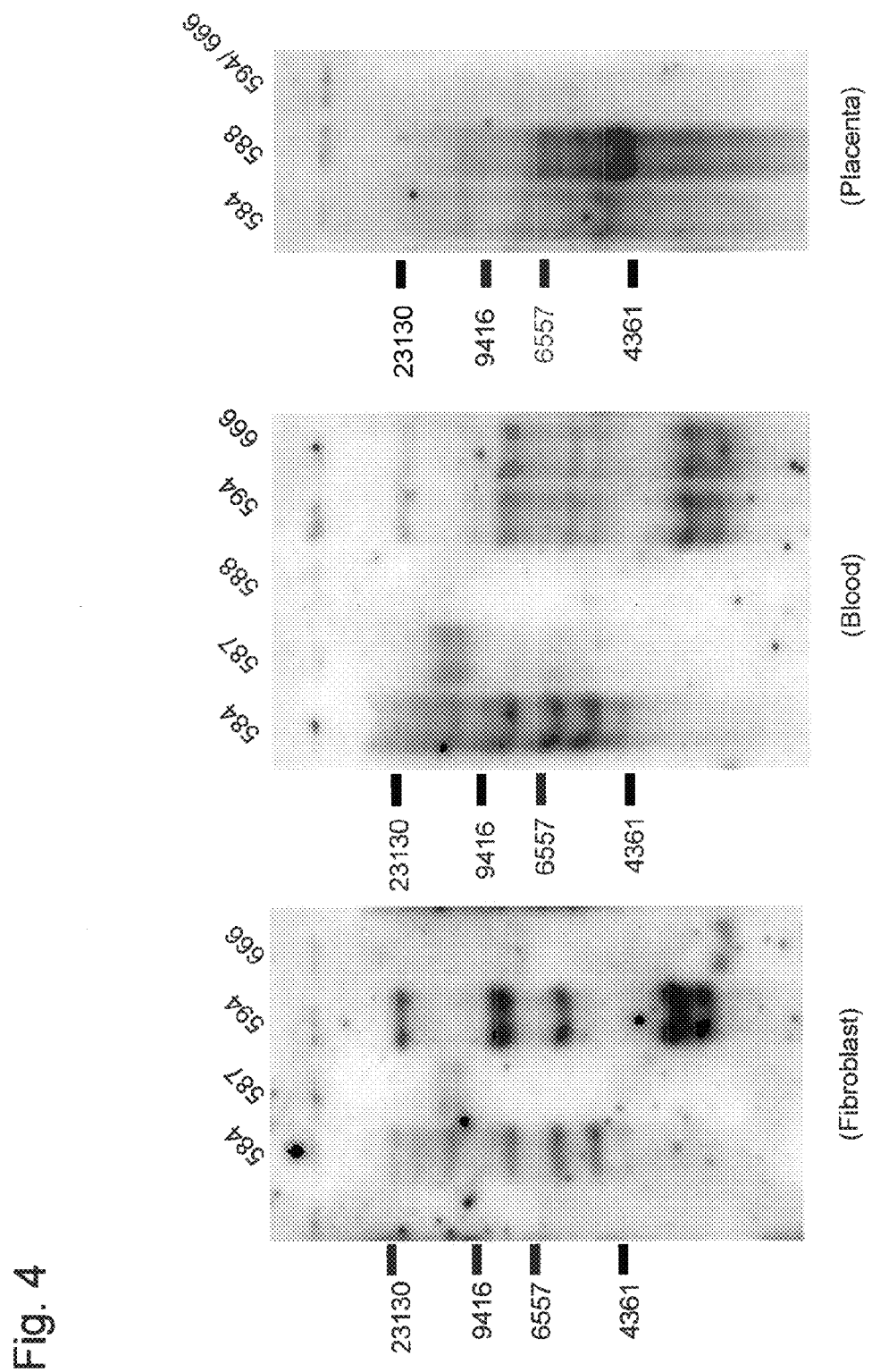
FIG. 4 shows photos showing the results of Southern blot analyses for samples extracted from the fibroblasts, blood, and placentae of transgenic common marmosets.

Southern blot analysis was conducted using DNA extracted from: cultured fibroblasts of skin sections of animals No. 584, No. 587, No. 594, and No. 666; blood of all 5 offspring; and placentae of animals No. 584, No. 588, and Nos. 594/666. Fibroblasts could not be obtained from No. 588 since they did not grow even when cultured. Southern blot analysis revealed that at least 4 copies of the transgene had been integrated into No. 584 and 2 copies of the transgene had been integrated into No. 587 (FIG. 4). Furthermore, integration of a plural number of copies of the transgene into the genome was confirmed in the fibroblasts and peripheral blood cells of No. 594 and No. 666 and the placenta of No. 588. In animal No. 588, transgene integration was observed only in the placenta. In Nos. 594/666, no transgene integration into the placenta was observed (FIG. 4).

To identify the chromosomal transgene integration sites, fluorescence in situ hybridization (FISH) was performed. Consistent with Southern blot, FISH results confirmed a plurality of integration sites in the chromosomes of peripheral blood lymphocytes. Moreover, all offspring were found to have several types of cells with different transgene integration patterns (Table 6). In animal No. 584, 4 transgene integration sites were observed on chromosomes 2, 7, 11, and 13. In No. 587, different signals were observed on chromosomes 3 and 12 of peripheral blood lymphocytes. No hybridization signals were observed in peripheral blood lymphocyte samples of No. 588, No. 594, and No. 666, which had a plurality of transgene integration patterns. Integration of at least 3 different types of transgene was found in animal No. 594, suggesting the presence of 6 or more patterns. Animal No. 666 was found to exhibit 13 integration patterns, which was the highest number. Of the 13 investigated karyotypes, 8 samples were of the female karyotype, owing to haematopoietic chimaerism caused by blood exchange with its twin, animal No. 594.

Figure 5:
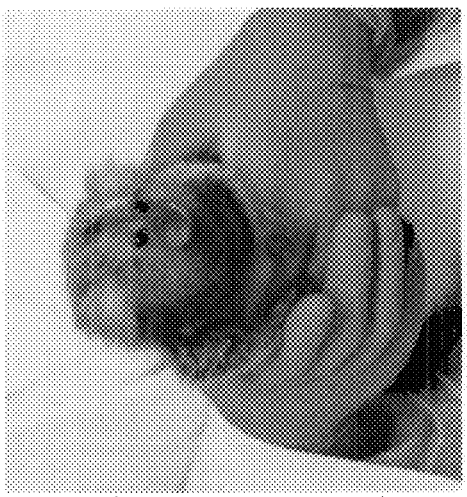
FIG. 5 shows photos of transgenic common marmosets that have been born.
Figure 5:
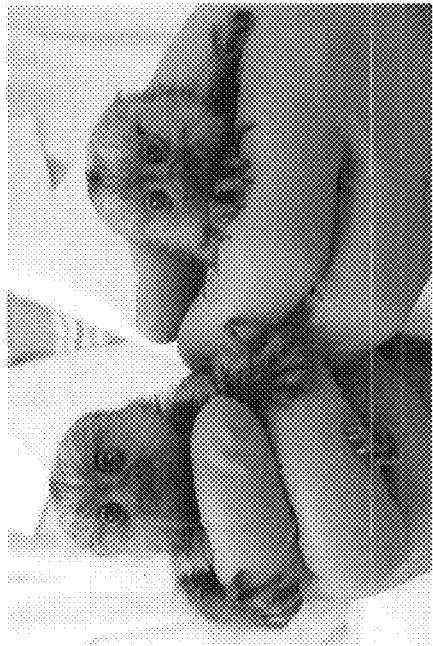
Figure 5:
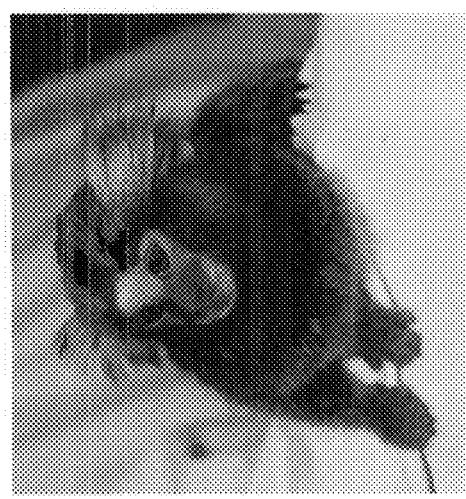
Figure 5:

FIG. 5 shows photos of the thus born transgenic common marmosets.

TABLE 5

| No. | Sample | EGFP transgene level[a] |
|---|---|---|
| 1 | Nega. I2443 Blood[b] | 1.0 (0.4 ± 2.8) |
| 2 | HISUI body hair | 36.1 (32.3 ± 40.4) |
| 3 | HISUI ear | 52.4 (44.8 ± 61.3) |
| 4 | HISUI blood | 53.9 (32.5 ± 89.6) |
| 5 | HISUI placenta | 85.9 (76.0 ± 97.2) |
| 6 | WAKABA body hair | 15.2 (14.0 ± 16.6) |
| 7 | WAKABA ear | 20.4 (16.4 ± 25.4) |
| 8 | WAKABA blood | 7.8 (6.8 ± 9.0) |
| 9 | BANKO body hair | 0.1 (0.1 ± 0.1) |
| 10 | BANKO ear | 0.1 (0.0 ± 0.1) |
| 11 | BANKO blood | 0.1 (0.0 ± 0.0) |
| 12 | BANKO placenta | 163.7 (128.5 ± 208.6) |
| 13 | KEI body hair | 432.0 (405.7 ± 460.0) |
| 14 | KEI ear | 352.7 (252.5 ± 492.7) |
| 15 | KEI blood | 39.4 (26.0 ± 59.6) |
| 16 | KEI, KOU placenta | 4.0 (1.8 ± 8.7) |
| 17 | KOU body hair | 51.6 (42.6 ± 62.5) |
| 18 | KOU ear | 34.9 (17.9 ± 68.2) |
| 19 | KOU blood | 220.2 (95.1 ± 509.8) |
| 20 | KEI, KOU placenta | 4.0 (1.8 ± 8.7) |

[a]Value relative to non-transgenic animal
[b]Negative control Non-transgenic marmoset (I2443) blood

TABLE 6

| Offspring No. | Sample No. | Transgene-integrated chromosome No. | | | |
|---|---|---|---|---|---|
| 584 | 001 | 2 | 7 | | 13 |
|  | 002 |  | 7 | | 13 |
|  | 003 | 2 | 7 | | 13 |
|  | 004 | 2 | 7 | | 13 |
|  | 005 | 1 | 3 | 7 | |
|  | 006 | 2 | 7 | 11 | 13 |
|  | 007 |  | 7 | | 13 |
|  | 008 | 2 | 7 | | 13 |
|  | 011 | 2 | 7 | 11 | 13 |
|  | 012 | 2 | 7 | 11 | 13 |
| 587 | 001 | 3 | 12 | | |
|  | 002 | 3 | | | |
|  | 003 | 3 | | | |
|  | 004 | 2 | 12 | | |
|  | 006 | 3 | | | |
|  | 007 | 3 | 12 | | |
|  | 008 | 3 | | | |
|  | 010 | 3 | 15 | | |
|  | 012 | 3 | | | |
|  | 013 | 3 | 12 | | |
| 588 | no signal | | | | |
| 594 | 001 | 4 | 5 | 7 | 14 |
|  | 002 | 1 | 2 | 5 | 7 |
|  | 201 | 1 | 2 | 3 | 5 | 11 |
|  | 202 | 5 | 12 | 19 | | |
|  | 302 | 2 | 4 | | | |
|  | 401 | 1 | 5 | 8 | | |
| 666 | 001 | 5 | 13 | | | |
|  | 002 | 2 | 22 | | | |
|  | 003 | 9 | | | | |
|  | 004 | 1 | 4 | 5 | | |
|  | 007 | 2 | 9 | 12 | 18 | |
|  | 008 | 2 | | | | |
|  | 301 | 2 | 5 | 7 | 9 | 11 |
|  | 310 | 1 | 5 | 12 | | |
|  | 202 | 11 | 22 | | | |
|  | 203 | 3 | 9 | 17 | 20 | |
|  | 205 | 1 | | | | |
|  | 303 | 2 | 20 X | | | |
|  | 313 | 1 | 9 | 12 | 20 | |

(3) Transgene Transcription and Expression

Figure 6:
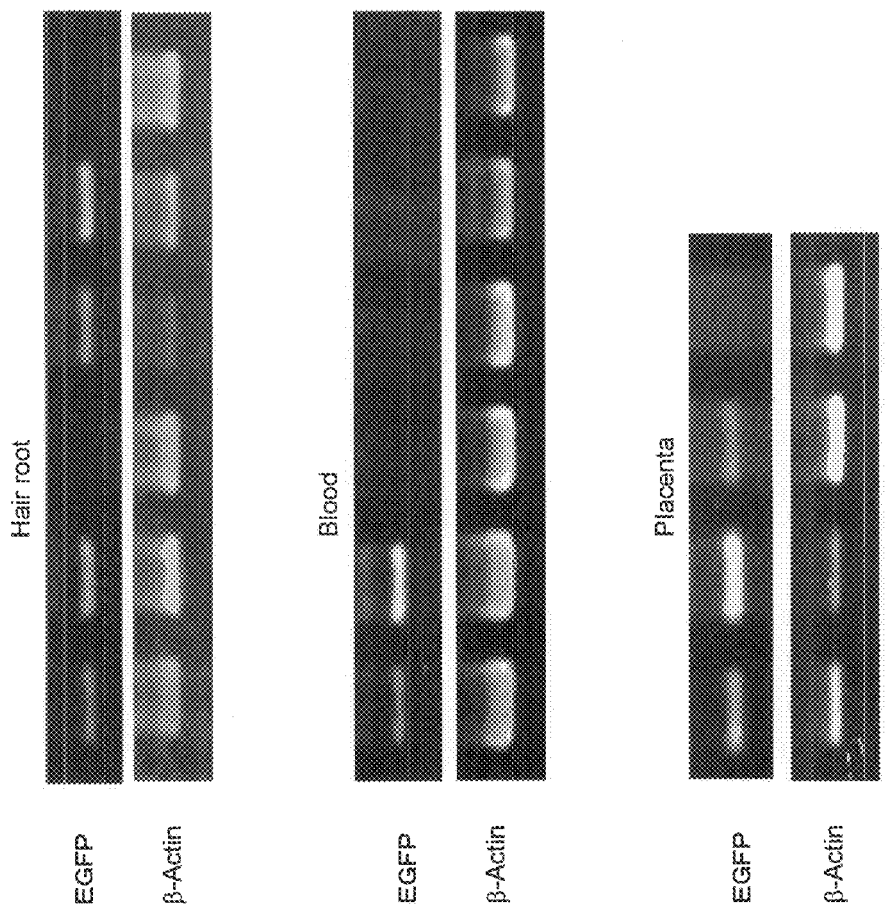
FIG. 6 shows photos showing EGFP transcription in the hair roots, blood, and placentae of transgenic common marmosets.

As a result of RT-PCR, transcription of EGFP gene mRNA was observed in the hair roots of all offspring excluding No. 588 and in the whole blood of No. 584 and No. 587. In placental samples, EGFP gene transcription was confirmed in all placental samples of No. 584, No. 588, and Nos. 594/666 (FIG. 6).

Figure 7:
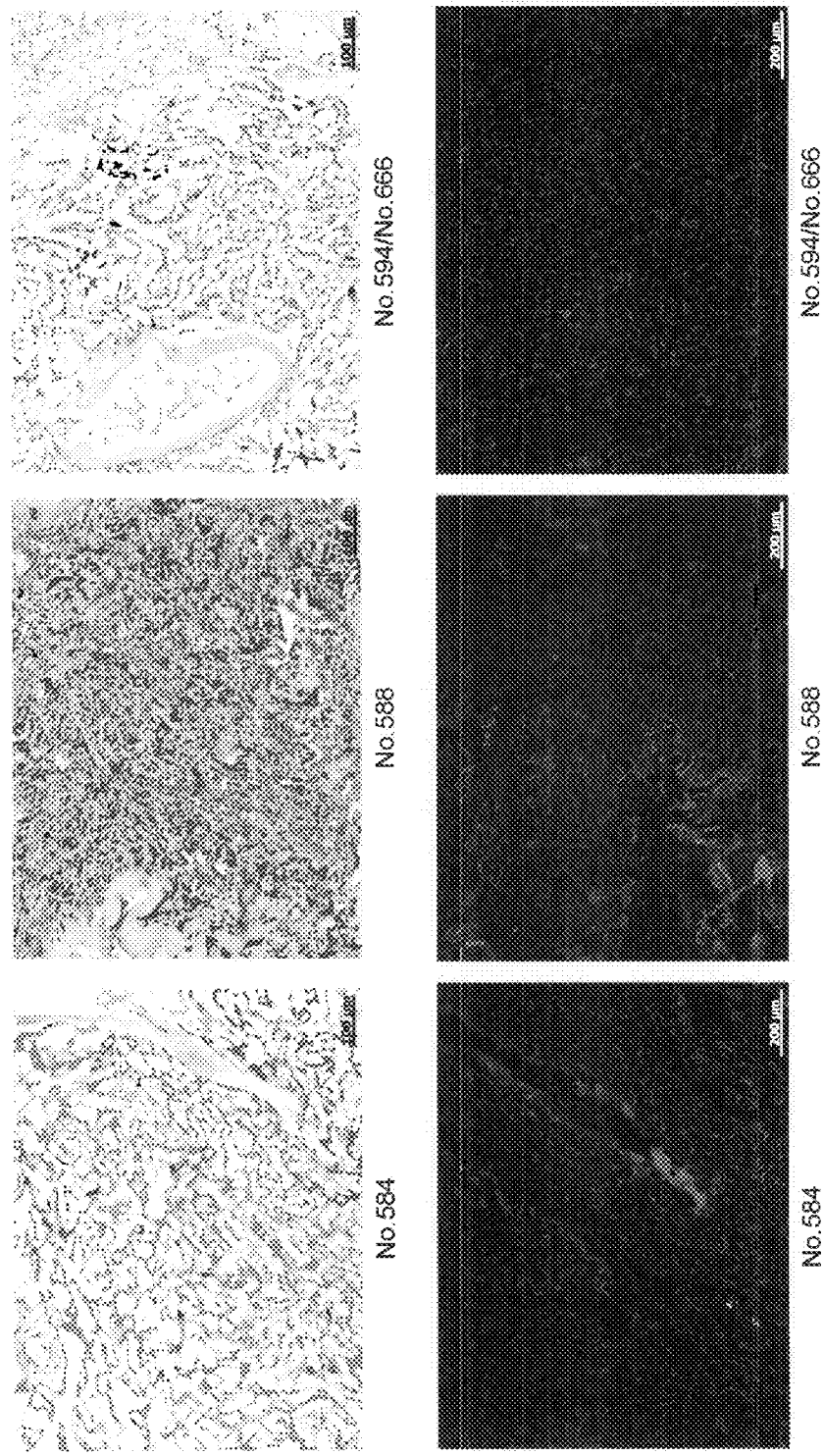
FIG. 7 shows photos showing EGFP expression in the placentae of transgenic common marmosets.
Figure 8:
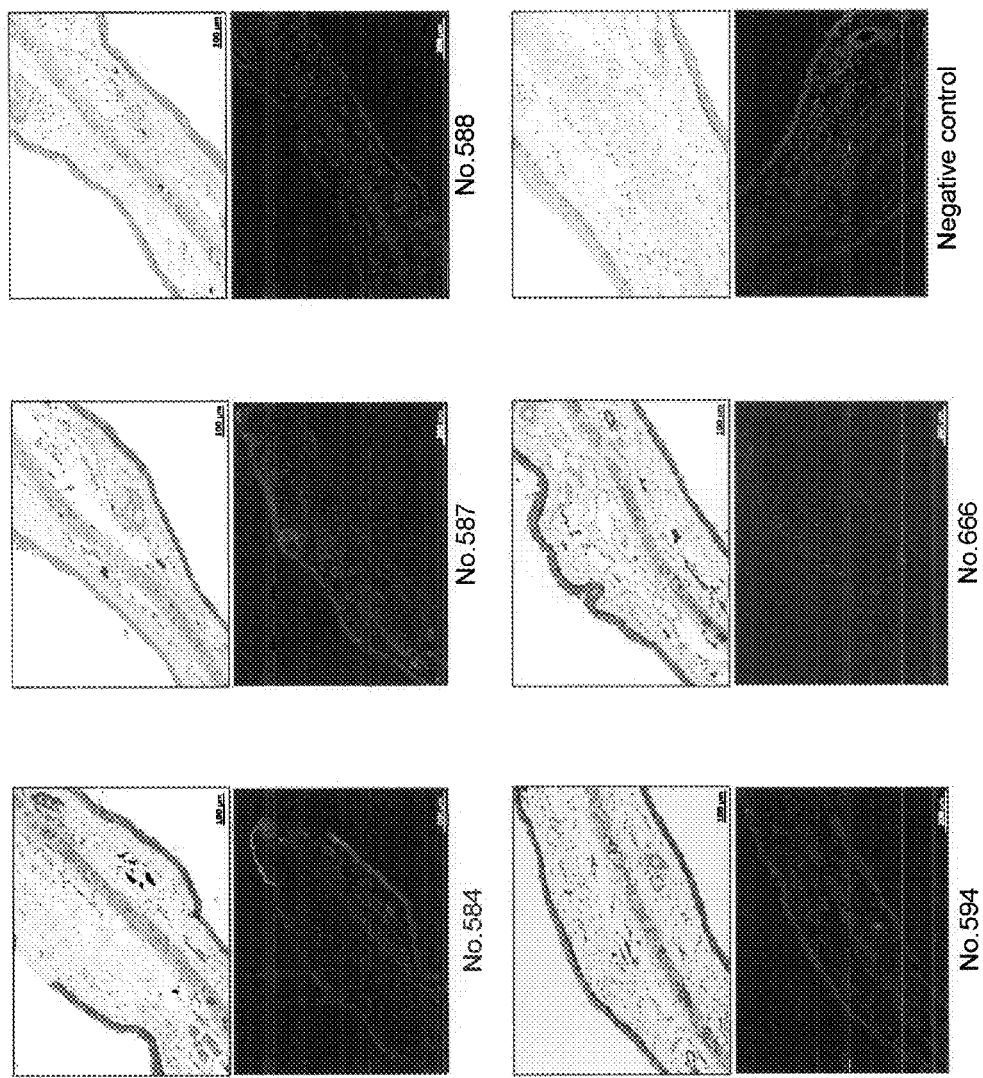
FIG. 8 shows photos showing EGFP expression in the ears of transgenic common marmosets.
Figure 9:
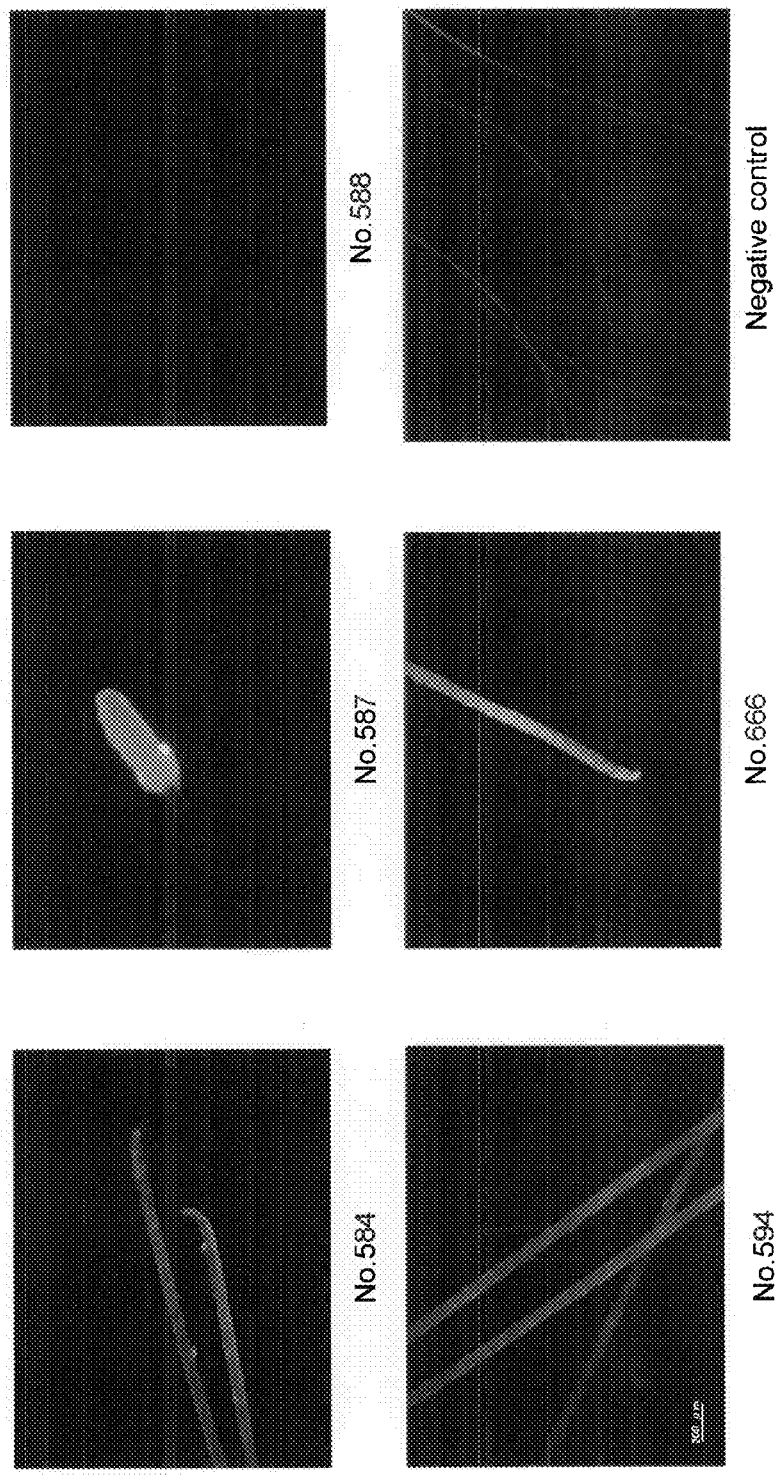
FIG. 9 shows photos showing EGFP expression in the hair roots of transgenic common marmosets.

EGFP fluorescence was directly detected by fluorescence microscopy using hair roots, skin sections, and placental samples. For preparation of section samples, small pieces of ear skin and placental samples were embedded in OCT Compound (sakura-finetek), frozen in liquid nitrogen, and then stored at −80° C. until analysis. To confirm EGFP expression in tissues, immunohistochemical analysis was conducted for small pieces of ear skin and placental tissue samples. Immunohistochemical analysis revealed that EGFP was strongly expressed in the ear skin and stromal cells of the placentae. In all the animals except No. 588, EGFP expression was observed in hair roots and skin. Placental samples from No. 584 and No. 588 showed EGFP expression at high levels, but no EGFP expression was detected in Nos. 594/666 (FIGS. 7, 8, and 9).

Figure 10:
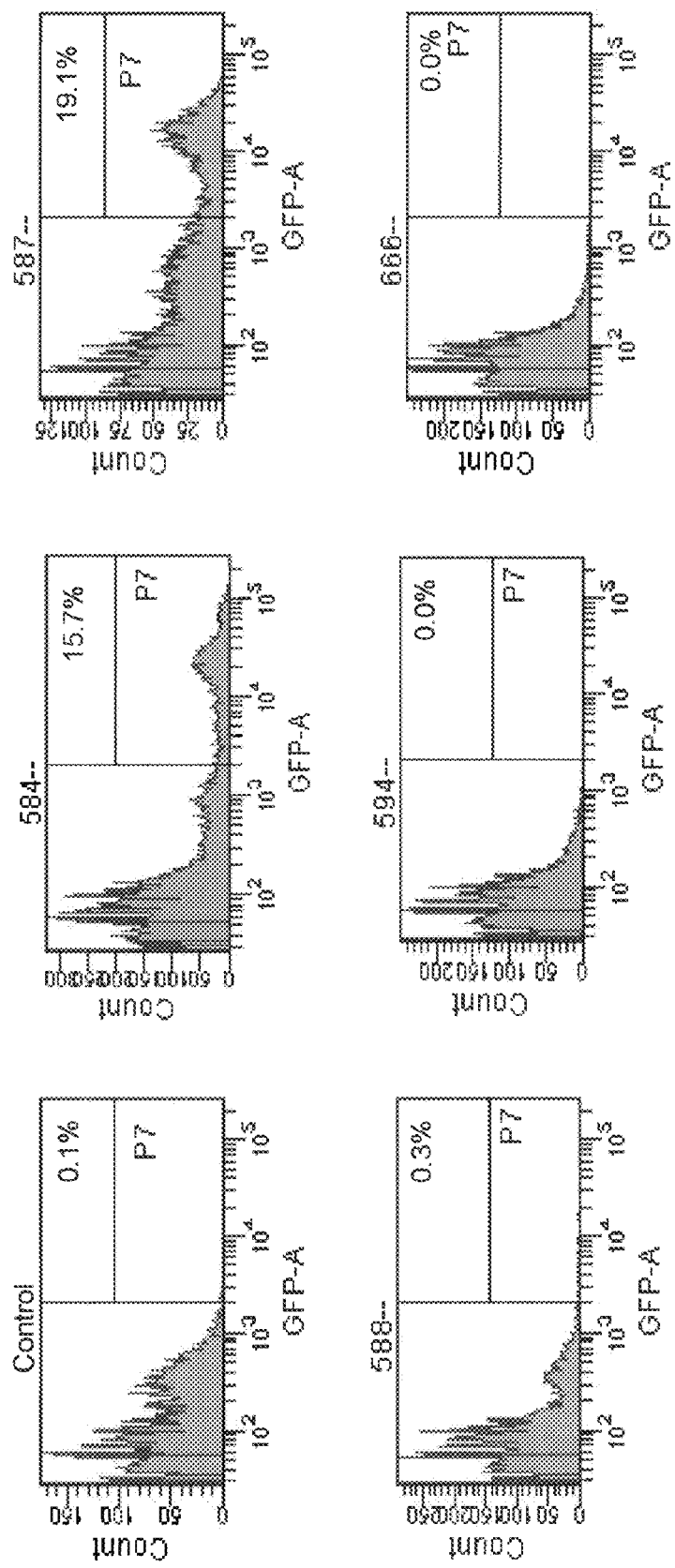
FIG. 10 shows the results of FACS analysis for the peripheral blood of transgenic common marmosets.

Peripheral blood samples were subjected to flow cytometric analysis (FACS). FACS analysis showed EGFP expression in the peripheral blood cells of No. 584 and No. 587. The expression levels thereof were 22.8% and 21.3%, respectively (FIG. 10). EGFP expression levels in these blood cells, granulocytes, lymphocytes, and macrophages were 43.4%, 15.9%, and 36.5%, respectively, in No. 584, and 47.7%, 9.25%, and 32.0%, respectively, in No. 587. The Results of FACS analysis corresponded to the result of RT-PCR.

As described above, it was demonstrated by the Examples that in 4 transgenic common marmosets, the transgene was not only integrated into somatic cells, but was expressed therein. The results of the Examples demonstrate that the SIN vectors used herein are effective for gene transfer for the production of transgenic common marmosets. Furthermore, in the Examples, lentiviral injection performed at as early an embryonic stage as possible also contributed to this success.

Technical differences between conventional methods and the method of the Examples are: the use of preimplantation embryos obtained by natural mating in the method of the Examples; the use of high-titer SIN vectors in the same; and the use of 0.25 M sucrose in the same.

Example 7

Germline Transmission in Transgenic Common Marmoset

The presence or the absence of germline transmission of the transgene was confirmed using the sexually mature transgenic common marmosets (#666 and #584) obtained in Example 6.

Semen samples were collected from animal #666, live spermatozoa were collected by the swim-up method in TYH medium, and then RT-PCR analysis was conducted. Subsequently, in vitro fertilization (IVF) was performed by the following method using semen collected from #666, and then the fertility of germ cells having the transgene was analyzed.

Oocytes treated with hyaluronidase were washed using TYH medium and then added to 70 μl of droplets. The 70 μl each of TYH droplets contained 10 oocytes at maximum. Ten (10) μL of semen was added to each oocyte incubation droplet. The final concentration of spermatozoa was $5 \times 10^6$ spermatozoa/mL. After 26 to 30 hours of fertilization, oocytes were removed from fertilized droplets and then washed with ISM1 medium (Medicult; Nosan). Fertilized embryos were cultured for 48 hours in ISM1 medium and then transferred to ISM2 (Nosan) medium containing feeder cells of mouse fetuses.

RT-PCR was performed by the following method.

Poly(A)+RNA was isolated from tissue samples using a Quick Prep Micro mRNA Purification Kit (GE Healthcare Biosciences). RNA samples were subjected to reverse transcription using an Improm-II Reverse Transcription System (Promega KK). Half of each poly(A)+RNA sample was reacted with reverse transcriptase for first strand cDNA synthesis. The other half was used as a negative control without reaction with reverse transcriptase. For germline transmission analysis, 2 to 8 embryos were used for RT-PCR. PCR was performed using 1/10 the first strand cDNA and a Prime STAR HS PCR enzyme (Takara Bio Inc.). PCR reaction was performed according to the manufacturer's protocols. For detection of EGFP gene expression, PCR was performed for 35 cycles each consisting of denaturing at 98° C. for 10 seconds, annealing at 60° C. for 10 seconds, and extension at 72° C. for 30 seconds. Primers used herein were EGFP5-4 (5'-CAAG-GACGACGGCAACTACAAGACC-3') (SEQ ID NO: 9) and EGFP3-3es (5'-GCTCGTCCATGCCGAGAGTGA-3') (SEQ ID NO: 10). Subsequently, 1/12.5 of the PCR product was amplified again using the primers, EGFP5-6 (5'-TC-GAGCTGAAGGGCATCGAC-3') (SEQ ID NO: 11) and EGFP3-1 (5'-TCACGAACTCCAGCAGGACCAT-3') (SEQ ID NO: 12). At this time, PCR was performed for 35 cycles each consisting of denaturing at 98° C. for 10 seconds, annealing at 60° C. for 10 seconds, and extension at 72° C. for 30 seconds. For detection of β-actin expression, PCR was performed for 35 cycles each consisting of denaturing at 94° C. for 10 seconds, annealing at 60° C. for 10 seconds, and extension at 72° C. for 30 seconds. Primers used herein were β-actin 003 (5'-TGGACTTCGAGCAGGAGAT-3') (SEQ ID NO: 13), β-actin 006R (5'-CCTGCTTGCTGATCCACATG-3') (SEQ ID NO: 14), and 005R (5'-GAGCCACCAATCCA-CACTGA-3') (SEQ ID NO: 15).

Figure 11:
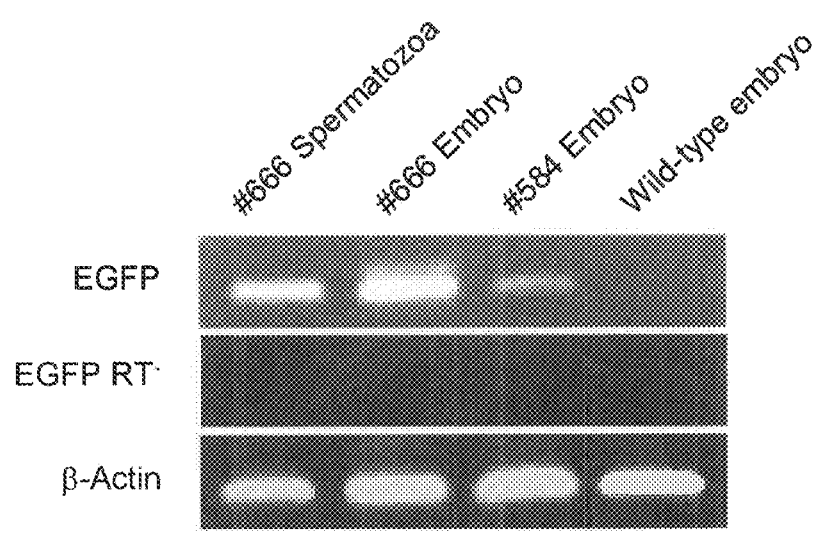
FIG. 11 shows photos showing the results of RT-PCR analysis for swim-up spermatozoa and IVF embryos from #666 and natural embryos from #584 and wild-type animals.

As a result, transgene transmission and expression were observed in germ cells of #666. FIG. 11 shows the results of RT-PCR analysis for swim-up spermatozoa and IVF embryos from #666, and natural embryos from #584 and wild-type animals. The top center shows the result of RT-PCR analysis using EGFP and the bottom shows the β-actin gene expressed as a control.

Figure 12:
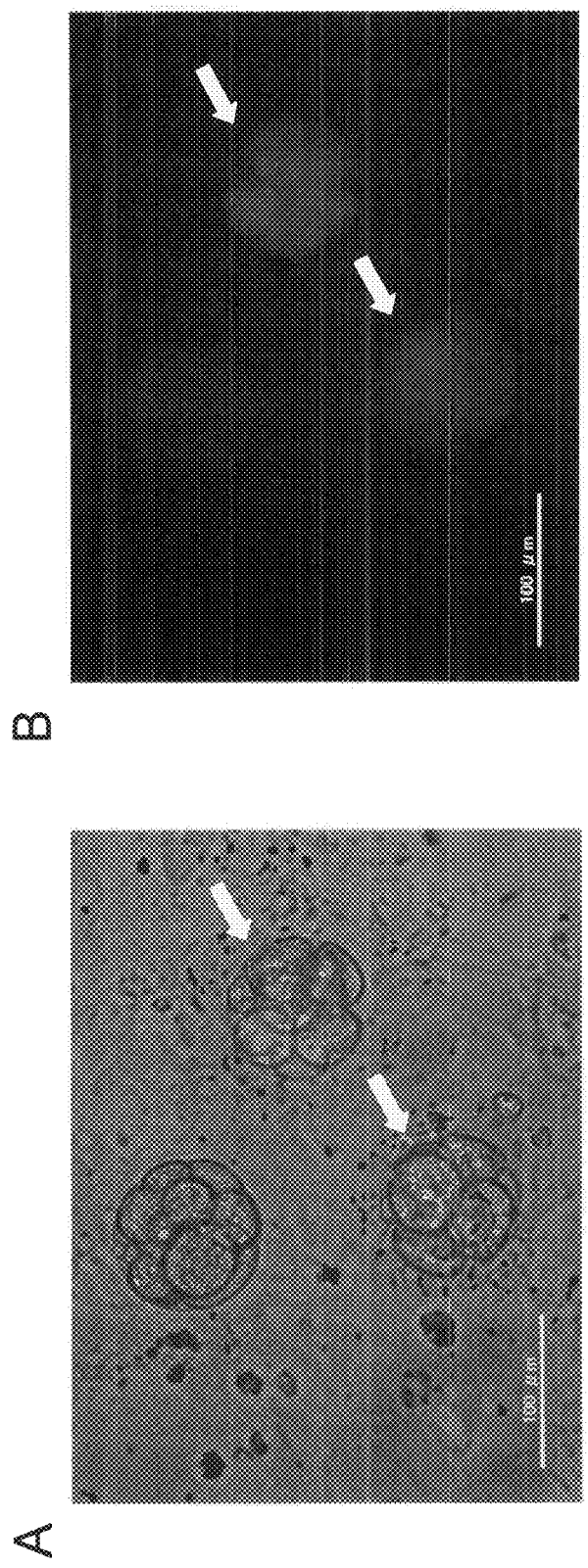
FIG. 12 shows photos showing bright fields and dark fields of epifluorescent microscopic analysis for IVF embryos.

Next, in vitro fertilization (IVF) was performed using semen collected from #666, and then the fertility of germ cells having the transgene was analyzed. It was revealed by fluorescence microscopy that 20% to 25% of embryos generated by IVF strongly expressed EGFP. FIG. 12 shows the bright field (A) and the dark field (B) of epifluorescence images obtained by epifluorescent microscopy performed for IVF embryos. Spermatozoa and IVF embryos of #666 are indicated by white arrows. The remaining embryos are wild-type embryos. Only the IVF embryos of #666 expressed EGFP. FIG. 12 shows high-level expression of EGFP by IVF embryos. Meanwhile, when 3 unimplanted live natural embryos were collected from #584 thereof, one of these embryos strongly expressed EGFP. It was confirmed by RT-PCR that IVF embryos from #666 and 2 natural blastocysts from #584 expressed the EGFP transgene.

Example 8

Figure 13:
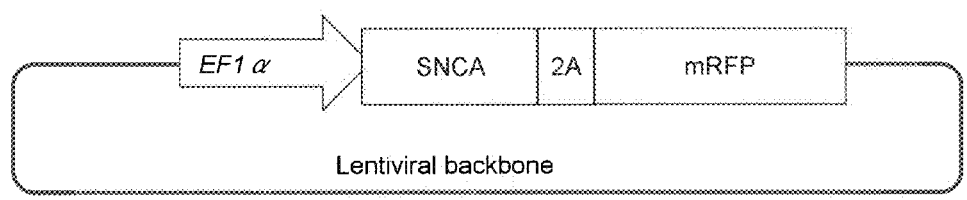
FIG. 13 shows the structure of a lentiviral vector containing a mutant α-synuclein gene.

Production of Parkinson's Disease Model Common Marmoset by Mutant α-Synuclein (SNCA) Overexpression In the case of human familial Parkinson's disease (PARK1), the α-synuclein gene is mutated and the α-Synuclein protein is mutated so that alanine (A) at position 30 of the amino acid sequence is mutated to proline (P) and alanine (A) at position 53 of the same is mutated to threonine (T). DNA complementary (cDNA) to the common marmoset α-synuclein gene was cloned, a mutant α-synuclein gene corresponding to a mutant α-synuclein gene of human familial Parkinson's disease was prepared, and then the marmoset mutant α-synuclein gene and a red fluorescent protein (mRFP) gene were flanked by 2 A peptide sequences downstream of an EF1α promoter, so that a lentiviral vector expressing a fusion protein of the two genes was constructed. At this time, EF1α was used as a promoter. FIG. 13 shows the structure of the lentiviral vector.

Figure 14:
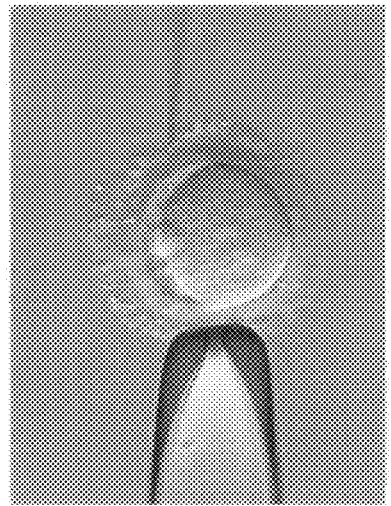
FIG. 14 shows photos showing in vitro fertilization (A) and the thus developed morulae (B and C).
Figure 14:
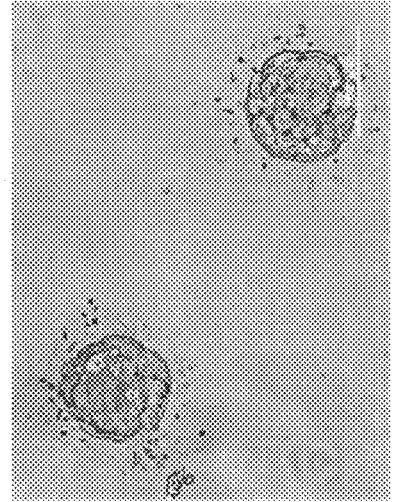
Figure 14:
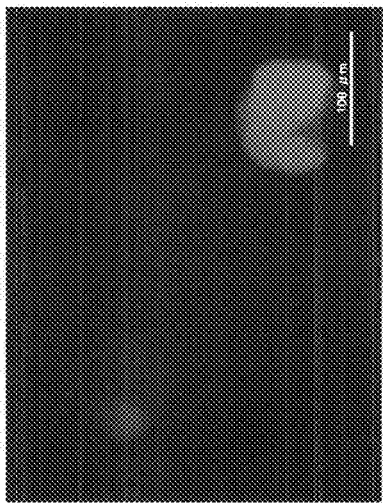

Ovarian stimulation, oocyte collection, and then in vitro maturation were performed by the methods described in Examples 1 and 2. A viral vector expressing a fusion protein of the common marmoset mutant α-synuclein gene and the red fluorescent protein mRFP gene flanked by 2 A peptide sequences was injected into the mature oocytes (obtained via IVM) at the MII stage in a 0.2 M-0.3 M sucrose solution. In vitro fertilization (IVF) was then performed. The mutant α-synuclein gene and the red fluorescent protein mRFP gene were separated after expression because of the 2 A peptides, so that the two proteins were expressed at a ratio of 1:1 in terms of molecular weight. Introduction of genes into oocytes at the MII stage enables production of transgenic animals with low mosaic rates. Under fluorescence microscopy, only morula fertilized eggs expressing red fluorescent protein were implanted in the uteri of surrogate common marmosets. FIG. 14 shows photos of in vitro fertilization (A) and the thus generated morula (B and C).

Figure 16:
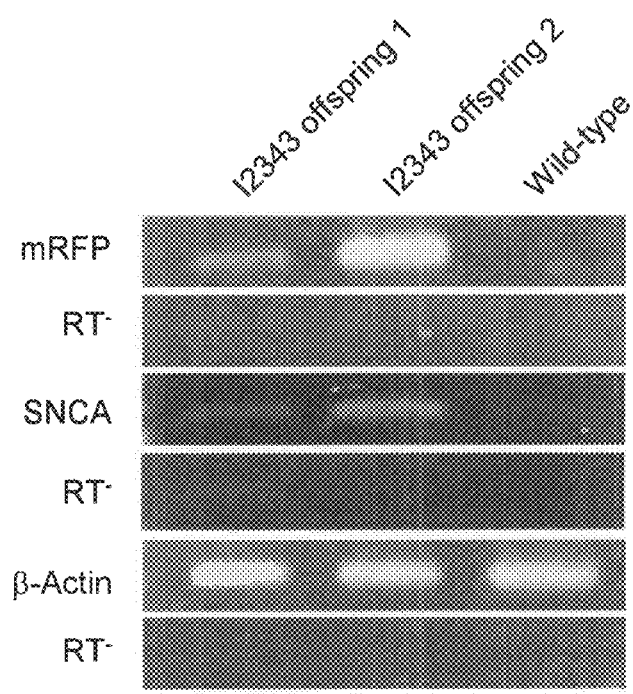
FIG. 16 shows photos showing the results of RT-PCR for root hair samples from the obtained offspring.
Figure 17:
FIG. 17 is a photo of obtained human Parkinson's disease model common marmosets.

As a result, two offspring were obtained. As a result of a parentage test using a common marmoset microsatellite marker, it was revealed that the offspring were derived from oocytes and spermatozoa donor animals. As a result of RT-PCR using hair root samples, the 2 obtained offspring expressed mRFP and the α-synuclein gene in the hair roots. Non-transgenic animals have the α-synuclein gene, but they do not express the gene in hair roots. Hence, there must be a difference between transgenic animals and non-transgenic animals. FIG. 15 shows the results of a parentage test using microlite markers. In FIG. 15, the two samples (12343 offspring 1 and 12343 offspring 2) shown in the lower two cases indicate offspring born. As shown in FIG. 15, the genotype of the 1CJ003-NED marker and that of the CJ091-FAM marker agreed with that of sample IH555, and the genotype of the CJ081-VIC marker agreed with that of 12991. This result indicates that the offspring that have been born were derived from the donors (12991 and IH555). FIG. 16 shows the results of RT-PCR for hair root samples from the thus obtained neonates. The left and the center lanes in FIG. 16 indicate hair root samples from neonates and the right lane indicates a sample from a wild-type common marmoset. FIG. 17 shows a photo of the thus obtained human Parkinson's disease model common marmoset.

INDUSTRIAL APPLICABILITY

According to the present invention, developmental engineering techniques are provided for producing transgenic primate animals such as transgenic marmosets that can be used as human disease model animals, for example. The use of the techniques of the present invention makes possible the efficient introduction of foreign genes into early embryos of primate animals, so that transgenic primate animals can be efficiently produced.

All publications, patents, and patent applications cited in this description are herein integrated by reference in their entirety.

The invention claimed is:

1. A method for introducing a human gene into a marmoset embryo comprising: placing a marmoset embryo that is between pronuclear and blastocyst stages into a 0.2 M-0.3 M sucrose solution thereby increasing the perivitelline space of the embryo, and injecting a lentiviral vector encoding a human gene operably linked to a promoter into the perivitelline space of the embryo.

2. The method of claim 1, wherein the volume of the perivitelline space increases 1.2- to 8-fold as compared to before sucrose treatment.

3. The method of claim 1, wherein the embryo is obtained by artificial insemination.

4. The method of claim 1, wherein the lentiviral vector has a titer ranging from $1.3 \times 10^3$ CFU to $1.3 \times 10^5$ CFU per embryo.

5. A method for making a transgenic marmoset expressing a human gene comprising:
   i) introducing a human gene into a marmoset embryo according to the method of claim 1;
   ii) implanting the embryo injected with the lentiviral vector into a recipient female marmoset; and
   iii) developing the embryo in the recipient female until a transgenic marmoset is obtained, wherein the transgenic marmoset has a genome comprising the lentiviral vector and expresses the human gene.

* * * * *